United States Patent
Barve et al.

(10) Patent No.: US 12,266,450 B1
(45) Date of Patent: Apr. 1, 2025

(54) APPARATUS AND METHODS FOR GENERATING ELECTRO-ANATOMICAL MAPPING

(71) Applicant: Anumana, Inc., Cambridge, MA (US)

(72) Inventors: Rakesh Barve, Bengaluru (IN); Suthirth Vaidya, Bengaluru (IN); Animesh Agarwal, San Mateo, CA (US); Abhijith Chunduru, Bengaluru (IN); Rohit Jain, Danville, CA (US)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/788,566

(22) Filed: Jul. 30, 2024

(51) Int. Cl.
| | |
|---|---|
| G16H 50/50 | (2018.01) |
| A61B 6/00 | (2006.01) |
| A61B 18/00 | (2006.01) |
| G06T 7/33 | (2017.01) |
| G06T 11/20 | (2006.01) |
| G16H 50/70 | (2018.01) |
| A61M 25/01 | (2006.01) |

(52) U.S. Cl.
CPC ............ G16H 50/50 (2018.01); A61B 6/5229 (2013.01); A61B 6/5247 (2013.01); A61B 18/00 (2013.01); G06T 7/33 (2017.01); G06T 11/206 (2013.01); G16H 50/70 (2018.01); A61B 2018/00577 (2013.01); A61B 2018/00839 (2013.01); A61M 2025/0166 (2013.01); G06T 2200/24 (2013.01); G06T 2207/20081 (2013.01); G06T 2210/41 (2013.01)

(58) Field of Classification Search
CPC ........... A61B 2018/00357; A61B 2018/00577; A61B 2018/00839; A61B 2505/05; A61B 2576/023; A61B 5/0035; A61B 5/0036; A61B 5/287; A61B 5/341; A61B 5/349; A61B 5/361; A61B 5/363; A61B 5/367; A61B 5/4848; A61B 5/7264; A61B 5/319; A61B 5/339; A61N 1/0563; A61N 1/362; A61N 1/3956; G16H 20/10; G16H 20/40; G16H 50/20; G16H 50/50; G16H 50/70

See application file for complete search history.

(56) References Cited

U.S. PATENT DOCUMENTS

| | | | |
|---|---|---|---|
| 7,715,604 B2 | 5/2010 | Sun et al. | |
| 2008/0228068 A1 | 9/2008 | Viswanathan et al. | |
| 2022/0061732 A1* | 3/2022 | Krummen | ............ A61B 5/0036 |
| 2023/0109856 A1 | 4/2023 | Shamilov et al. | |
| 2023/0363643 A1 | 11/2023 | Tran | |

* cited by examiner

*Primary Examiner* — Manuchehr Rahmjoo
(74) *Attorney, Agent, or Firm* — Caldwell Intellectual Property Law

(57) ABSTRACT

Apparatus for generating electro-anatomical mapping and methods used therein include a processor and a memory connected to the processor, wherein the memory contains instructions configuring the processor to receive input data, generate, using at least a machine learning model, an electro-anatomical mapping as a function of the input data, and display the electro-anatomical mapping using a user interface, wherein receiving the input data includes receiving, from an imaging device, at least a medical image and receiving, from a signal capturing device, at least an electrogram, wherein the at least a machine learning model is trained using electro-anatomical mapping training data including exemplary medical images and exemplary electrograms as input correlated to exemplary electro-anatomical mappings as output.

26 Claims, 9 Drawing Sheets

APPARATUS AND METHODS FOR GENERATING ELECTRO-ANATOMICAL MAPPING

FIELD OF THE INVENTION

The present invention generally relates to the field of medical imaging and clinical decision support. In particular, the present invention is directed to apparatus and methods for generating electro-anatomical mapping.

BACKGROUND

Electro-anatomical mapping is a sophisticated diagnostic tool that merges electrical activity data with anatomical imaging to create a detailed, 3D representation of the conduction system within an organ or a tissue. It is often used to accurately diagnose and treat cardiac arrhythmias by providing clinicians with precise information about the heart's electrical pathways and structural features. However, traditional electro-anatomical mapping techniques also require specialized medical facilities such as Electrophysiology Labs. Additionally, these techniques often involve invasive and potentially harmful procedures such as insertion of catheters and exposure to X-rays. As a result, patients undergoing such procedures often need to endure high costs as well as significant risk and discomfort.

SUMMARY OF THE DISCLOSURE

In an aspect, an apparatus for generating electro-anatomical mapping is described. Apparatus includes a processor and a memory communicatively connected to the processor, wherein the memory contains instructions configuring the processor to receive input data, wherein receiving the input data includes receiving, from an imaging device, at least a medical image and receiving, from a signal capturing device, at least an electrogram. Processor is further configured to generate, using at least a machine learning model, an electro-anatomical mapping as a function of input data, wherein the at least a machine learning model is trained using electro-anatomical mapping training data including exemplary medical images and exemplary electrograms as input correlated to exemplary electro-anatomical mappings as output. Processor is further configured to display electro-anatomical mapping using a user interface.

In another aspect, a method for generating electro-anatomical mapping is described. Method is performed by processor and includes receiving input data, wherein receiving the input data includes receiving, from imaging device, at least a medical image and receiving, from signal capturing device, at least an electrogram. Method further includes generating, using at least a machine learning model, electro-anatomical mapping as a function of the input data, wherein the at least a machine learning model is trained using electro-anatomical mapping training data including exemplary medical images and exemplary electrograms as input correlated to exemplary electro-anatomical mappings as output. Method further includes displaying, using user interface, electro-anatomical mapping.

These and other aspects and features of nonlimiting embodiments of the present invention will become apparent to those skilled in the art upon review of the following description of specific nonlimiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

Figure 1A:
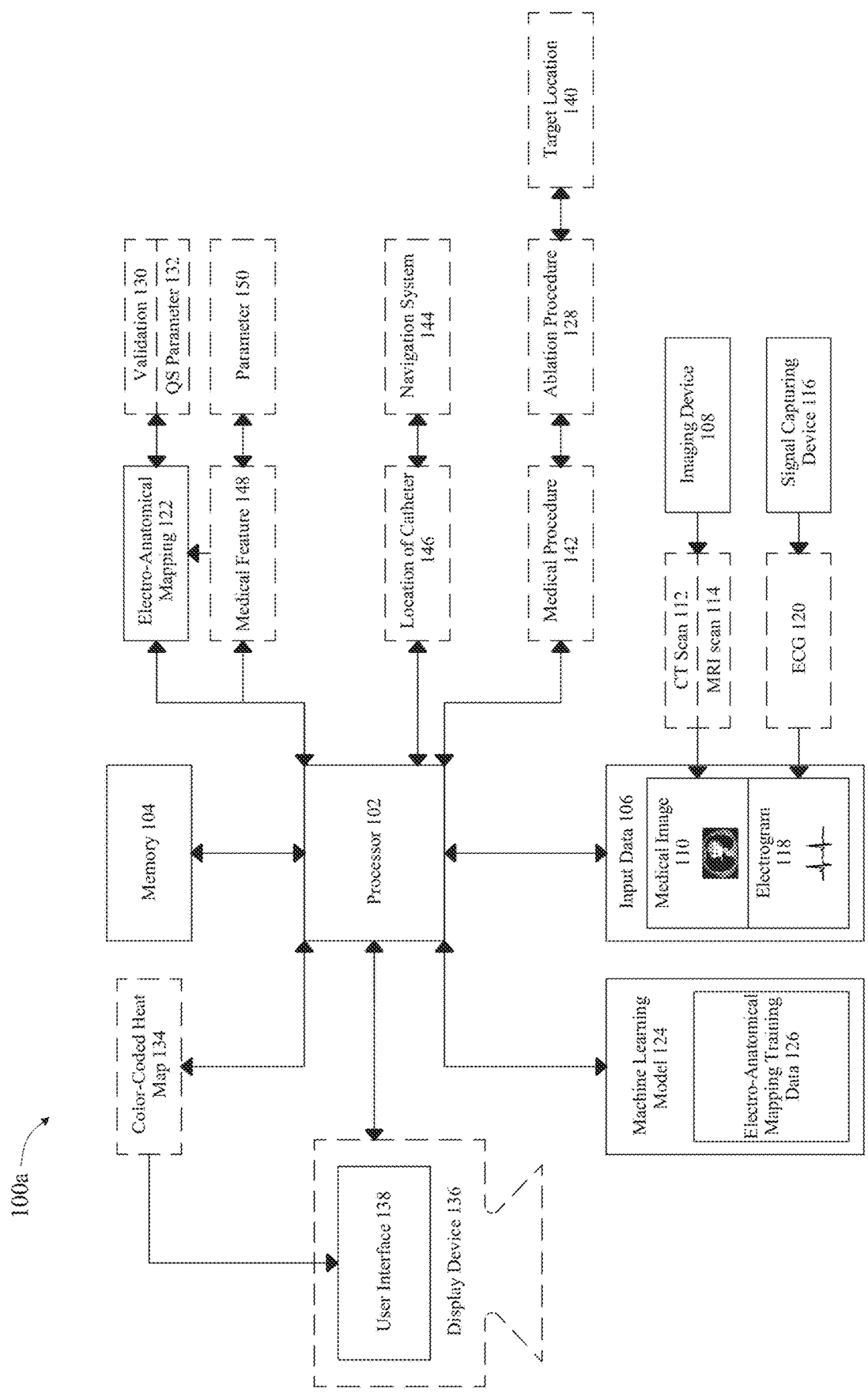
FIG. 1A is an exemplary embodiment of an apparatus for generating an electro-anatomical mapping.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatus and methods for generating electro-anatomical mapping. Apparatus includes a processor and a memory communicatively connected to the processor, wherein the memory contains instructions configuring the processor to receive input data, wherein receiving the input data includes receiving, from an imaging device, at least a medical image and receiving, from a signal capturing device, at least an electrogram. In one or more embodiments, at least a medical image may include at least a computed tomography (CT) scan and/or at least a magnetic resonance imaging (MRI) scan. In one or more embodiments, at least an electrogram may include at least an electrocardiogram (ECG). In some cases, input data and/or at least a medical image may include ultrasound data. Processor is further configured to generate, using at least a machine learning model, an electro-anatomical mapping as a function of input data, wherein the at least a machine learning model is trained using electro-anatomical mapping training data including exemplary medical images and exemplary electrograms as input correlated to exemplary electro-anatomical mappings as output. In one or more embodiments, exemplary medical images may include historical medical images pertaining to a plurality of entities and collected prior to one or more historical medical procedures. In one or more embodiments, exemplary electrograms may include historical electrograms pertaining to plurality of entities, wherein the historical electrograms are collected prior to one or more historical medical procedures and temporally correlated with exemplary medical images. In one or more embodiments, exemplary electro-anatomical mappings may include historical electro-anatomical mappings pertaining to plurality of entities and collected during one or more historical medical procedures. In one or more embodiments, generating electro-anatomical mapping may include generating a putative electro-anatomical mapping, validating the putative electro-anatomical mapping using a plurality of quality assurance parameters, and creating the electro-anatomical mapping by fine-tuning the putative electro-anatomical mapping as a function of an outcome of the validation. In one or more embodiments, electro-anatomical mapping may include a color-coded heat map. Processor is further configured to display electro-anatomical mapping using a user interface. In one or more embodiments, processor may be further configured to identify at least a target location pertaining to a medical procedure within electro-anatomical mapping and highlight the at least a target location within the electro-anatomical mapping using user interface. In some cases, medical procedure may include an ablation procedure and electro-anatomical mapping is used as an initial mapping for the ablation procedure. In some cases, processor is further configured to receive, from a navigation system, a location of a catheter and display, using user interface, the location of the catheter on electro-anatomical mapping. In some cases, processor may be further configured modify electro-anatomical mapping as a function of location of catheter. In some cases, processor may be further configured to identify at least a medical feature within electro-anatomical mapping and adjust at least a parameter pertaining to medical procedure as a function of the at least a medical feature. In one or more embodiments, generating electro-anatomical mapping may include aligning an electrical mapping with an anatomical mapping using fiducial point-based registration.

Aspects of the present disclosure may be used to provide safe, affordable, and efficient clinical decision support. Aspects of the present disclosure may be used to provide real-time, adaptive guidance during medical procedures, such as cardiac ablation, without exposing patients to repeated discomfort. Aspects of the present disclosure may be used to promote the use of noninvasive or minimally invasive clinical tools for such medical procedures. Aspects of the present disclosure may be used to support image-guided surgery and therapy. Exemplary embodiments illustrating aspects of the present disclosure are described below in the context of several specific examples.

Referring now to FIG. 1A, an exemplary embodiment 100a of an apparatus 100 for generating electro-anatomical mapping is illustrated. Apparatus 100 includes a processor 102. In one or more embodiments, processor 102 may include a computing device. Computing device could include any analog or digital control circuit, including an operational amplifier circuit, a combinational logic circuit, a sequential logic circuit, an application-specific integrated circuit (ASIC), a field programmable gate arrays (FPGA), or the like. Computing device may include a processor communicatively connected to a memory, as described above. Computing device may include any computing device as described in this disclosure, including without limitation a microcontroller, microprocessor, digital signal processor, and/or system on a chip as described in this disclosure. Computing device may include, be included in, and/or communicate with a mobile device such as a mobile telephone, smartphone, or tablet. Computing device may include a single computing device operating independently, or may include two or more computing device operating in concert, in parallel, sequentially, or the like; two or more computing devices may be included together in a single computing device or in two or more computing devices. Computing device may interface or communicate with one or more additional devices as described below in further detail via a network interface device. Network interface device may be utilized for connecting computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device may include but is not limited to, for example, a first computing device or cluster of computing devices in a first location and a second computing device or cluster of computing devices in a second location. Computing device may include one or more computing devices dedicated to data storage, security, distribution of traffic for load balancing, and the like. Computing device may distribute one or more computing tasks as described below across a plurality of computing devices of computing device, which may operate in parallel, in series, redundantly, or in any other manner used for distribution of tasks or memory between computing devices. Computing device may be implemented, as a non-limiting example, using a "shared nothing" architecture.

With continued reference to FIG. 1A, computing device may be designed and/or configured to perform any method, method step, or sequence of method steps in any embodiment described in this disclosure, in any order and with any degree of repetition. For instance, computing device may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. A person of ordinary skill in the art, upon reviewing the entirety of this disclosure, will be aware of various ways in which steps, sequences of steps, processing tasks, and/or data may be subdivided, shared, or otherwise dealt with using iteration, recursion, and/or parallel processing. More details regarding computing devices will be described below.

With continued reference to FIG. 1A, apparatus 100 includes a memory 104 communicatively connected to processor 102, wherein the memory 104 contains instructions configuring the processor 102 to perform any processing steps described herein. For the purposes of this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, using a bus or other facility for intercommunication between elements of a computing device. Communicative connecting may also include indirect connections via, for example and without limitation, wireless connection, radio communication, low-power wide-area network, optical communication, magnetic, capacitive, or optical coupling, and the like. In some instances, the terminology "communicatively coupled" may be used in place of communicatively connected in this disclosure.

With continued reference to FIG. 1A, computing device may perform determinations, classification, and/or analysis steps, methods, processes, or the like as described in this disclosure using machine learning processes. For the purposes of this disclosure, a "machine learning process" is a process that automatedly uses a body of data known as "training data" and/or a "training set" to generate an algorithm that will be performed by a processor module to produce outputs given data provided as inputs. This is in contrast to a nonmachine learning software program where the commands to be executed are determined in advance by a user and written in a programming language. A machine learning process may utilize supervised, unsupervised, lazy-learning processes and/or neural networks. More details regarding computing devices and machine learning processes will be provided below.

With continued reference to FIG. 1A, apparatus 100 may include or be communicatively connected to a database. For the purposes of this disclosure, a "database" is an organized collection of data or a type of data store based on the use of a database management system (DBMS), the software that interacts with end users, applications, and the database itself to capture and analyze the data. Database may be implemented, without limitation, as a relational database, a key-value retrieval database such as a NoSQL database, or any other format or structure for use as database that a person of ordinary skill in the art would recognize as suitable upon review of the entirety of this disclosure. Database may Alternatively, and/or additionally, be implemented using a distributed data storage protocol and/or data structure, such as a distributed hash table or the like. Database may include a plurality of data entries and/or records as described in this disclosure. Data entries in database may be flagged with or linked to one or more additional elements of information, which may be reflected in data entry cells and/or in linked tables such as tables related by one or more indices in database or another relational database. A person of ordinary skill in the art, upon reviewing the entirety of this disclosure, will be aware of various ways in which data entries in database may store, retrieve, organize, and/or reflect data and/or records as used herein, as well as categories and/or populations of data consistently with this disclosure.

With continued reference to FIG. 1A, apparatus 100 may include or be communicatively connected to one or more electronic health records (EHRs). For the purposes of this disclosure, an electronic health record (EHR) is a comprehensive collection of records relating to the health history, diagnosis, or condition of a patient, relating to treatment provided or proposed to be provided to the patient, or relating to additional factors that may impact the health of the patient; elements within an EHR, once combined, may provide a detailed picture of patient's overall health. In one or more embodiments, medical information such as medical images may be deposited to and retrieved from one or more EHRs. In one or more embodiments, EHR may include demographic data of patient; for example, and without limitation, EHR may include basic information about patient such as name, age, gender, ethnicity, socioeconomic status, and/or the like. In one or more embodiments, each EHR may also include patient's medical history; for example, and without limitation, EHR may include a detailed record of patient's past health conditions, medical procedures, hospitalizations, and illnesses such as surgeries, treatments, medications, allergies, and/or the like. In one or more embodiments, each EHR may include lifestyle information of patient; for example, and without limitation, EHR may include details about the patient's diet, exercise habits, smoking and alcohol consumption, and other behaviors that could impact patient's health. In one or more embodiments, EHR may include patient's family history; for example, and without limitation, EHR may include a record of hereditary diseases. In one or more embodiments, database may comprise a plurality of EHRs. In one or more embodiments, EHRs may be retrieved from a repository of similar nature as database.

With continued reference to FIG. 1A, processor 102 is configured to receive input data 106. For the purposes of this disclosure, "input data" are data or information that may be used as input to initiate subsequent processing steps. Input data 106 may include any type or form of data that contain medically relevant information, as recognized by a person of ordinary skill in the art upon reviewing the entirety of this disclosure. Apparatus 100 may include or be communicatively connected to imaging device 108. Accordingly, receiving input data 106 includes receiving, from imaging device 108, at least a medical image 110. For the purposes of this disclosure, an "imaging device" is a device capable of recording a digital representation of an object. Imaging device 108 may include any type of imaging device accessible to a person of ordinary skill in the art, and/or deemed suitable by a person of ordinary skill in the art upon reviewing the entirety of this disclosure. In one or more embodiments, imaging device 108 may include a camera. For the purposes of this disclosure, a "camera" is a single device, or an assembly of multiple devices, configured to detect at least one type of electromagnetic radiation and generate a graphical representation therefrom. As nonlimiting examples, a camera may detect visible light, infrared light, ultraviolet light, or X-ray. In one or more embodiments, a camera may include one or more optics. Nonlimiting examples of optics include spherical lenses, aspherical lenses, reflectors, polarizers, filters, windows, aperture stops, and the like. In one or more embodiments, a camera may include an image sensor. Exemplary image sensors include digital image sensors, such as without limitation charge-coupled device (CCD) sensors and complimentary metal-oxide-semiconductor (CMOS) sensors. As a nonlimiting example, a camera may include a remote camera device communicatively connected to a computing device, such as a portable camera connected to a desktop or laptop computer through either a cord or wireless connection. As another nonlimiting example, a camera may include a built-in camera integrated within a computing device, such as a built-in camera of a laptop computer. As another nonlimiting example, a camera may include a built-in camera integrated within a remote and/or portable device, such as a built-in camera of a smartphone or a tablet.

With continued reference to FIG. 1A, for the purposes of this disclosure, a "medical image" is an image containing medically relevant features or information. In one or more embodiments, at least a medical image 110 may include one or more computed tomography (CT) images or scans 112. For the purposes of this disclosure, computed tomography (CT) is a medical imaging technique that uses X-rays to capture cross-sectional images (slices) of a patient's body. By taking a plurality of slices, a CT scan creates a detailed three-dimensional (3D) representation of internal structures. In one or more embodiments, at least a medical image 110 may include at least a magnetic resonance imaging (MRI) scan 114. For the purposes of this disclosure, "magnetic resonance imaging (MRI)" is a noninvasive diagnostic technique that utilizes a combination of strong magnetic fields and radiofrequency waves to generate detailed images of the internal structures of an organ or a tissue. MRI typically involves placing a subject within a magnetic field, aligning the nuclear magnetization of hydrogen atoms in the body of the subject. Radiofrequency pulses are then applied to perturb this alignment. As hydrogen atoms relax back to their ground state, the emitted energy therefrom is captured to construct high-resolution images based on varying tissue densities and compositions. MRI is extensively used for visualizing soft tissues, including the brain, muscles, and cardiovascular structures.

With continued reference to FIG. 1A, for the purposes of this disclosure, an "image" is a visual representation of data. In one or more embodiments, an image may be a product of imaging device described above. In one or more embodiments, an image may contain digital information representing at least a physical scene, space, and/or object. In one or more embodiments, an image may be an optical image, such as without limitation an image of an object generated by at least an optic. In some cases, an image may be a digital representation of another image, such as a digital image of a printed photograph or the like captured using a built-in camera of a smartphone. Alternatively, an image may include a plurality of images arranged in sequence as a function of time, such as one or more videos. In some cases, an image may include a digital image. A digital image may be in a format such as jpeg, png, pdf, btmp, and the like.

With continued reference to FIG. 1A, apparatus 100 may include or be communicatively connected to a signal capturing device 116. Accordingly, receiving input data 106 includes receiving, from signal capturing device 116, at least an electrogram 118. For the purposes of this disclosure, a "signal capturing device" is a device capable of capturing a signal and one or more features therein. For the purposes of this disclosure, a "signal" is an intelligible representation of data that's transmitted from one device to another. A signal may include an optical signal, a hydraulic signal, a pneumatic signal, a mechanical signal, an electric signal, a digital signal, an analog signal, and the like. In some cases, a signal may be used to communicate with a computing device, for example by way of one or more ports. In some cases, a signal may be transmitted and/or received by a computing device, for example, by way of an input/output port. An analog signal may be digitized, for example by way of an analog to digital converter. In some cases, an analog signal may be processed, for example by way of any analog signal processing steps described in this disclosure, prior to digitization. In some cases, a digital signal may be used to communicate between two or more devices, including without limitation computing devices. In some cases, a digital signal may be communicated by way of one or more communication protocols, including without limitation internet protocol (IP), controller area network (CAN) protocols, serial communication protocols (e.g., universal asynchronous receiver-transmitter [UART]), parallel communication protocols (e.g., IEEE 128 [printer port]), and the like.

With continued reference to FIG. 1A, for the purposes of this disclosure, an "electrogram" is a diagnostic recording obtained from electrodes placed directly on or within one or more organs or tissues to measure their electrical activity. This recording captures the temporal sequence of electrical potentials generated by a conduction system of such organs or tissues, providing detailed information about their electrical behaviors. In addition to the heart, organs such as the brain, skeletal muscles, nerves, eyes, stomach, intestines, uterus, and bladder may also exhibit electrical activities. These activities are essential for various physiological functions and may be measured using specific diagnostic techniques such as electroencephalography (EEG), electromyography (EMG), nerve conduction studies (NCS), electroretinography (ERG), electrogastrography (EGG), and urodynamic studies, among others. As a nonlimiting example, for the heart, electrograms 118 may be utilized to identify and analyze arrhythmias, guide therapeutic interventions such as catheter ablation, and assess the effectiveness of treatments. The data acquired from electrograms 118 is crucial for diagnosing and managing various cardiac conditions, offering a precise and localized view of cardiac electrical activity. Additional details will be provided below.

With continued reference to FIG. 1A, in one or more embodiments, at least an electrogram 118 may include at least an electrocardiogram (ECG) 120. For the purposes of this disclosure, an "electrocardiogram (ECG)" is a recording of electrical activity of patient's heart over a period of time; "ECG" and "ECG data" may be used interchangeably throughout this disclosure. In one or more embodiments, ECG data may include one or more recordings captured by a plurality (e.g., 12) of electrodes placed on patient's skin. In one or more embodiments, ECG data may include information regarding a P wave, T wave, QRS complex, PR interval, ST segment, and/or the like, as described in detail below in this disclosure. In one or more embodiments, ECG data may be used to identify specific cardiac events or phases of a cardiac cycle, e.g., isovolumic relaxation, ventricular filling, isovolumic contraction, and rapid ventricular ejection. In one or more embodiments, at least an electrogram 118 may include at least an electroencephalogram (EEG). For the purposes of this disclosure, an "electroencephalogram (EEG)" is an electrogram of the spontaneous electrical activity of the brain measured using small, metal discs (electrodes) attached to the scalp; it provides useful diagnostic information related to brain disorders.

With continued reference to FIG. 1A, in one or more embodiments, apparatus 100 may include or be communicatively connected to an ultrasonic imaging system. For the purposes of this disclosure, an "ultrasonic imaging system" is an image capture device capable of capturing at least an ultrasound image. In some cases, ultrasonic imaging system may render a graphic representation of a three-dimensional (3D) object by sending ultrasound waves and detecting their reflections as they interact with a plurality of features or structures with various values of density and/or reflectivity within the 3D object. In some cases, 3D object may include an organ such as the heart with complex internal structures including walls, chambers, blood vessels, among others. In some cases, ultrasonic imaging system may include at least an ultrasound transducer. For the purposes of this disclosure, an "ultrasound transducer" is a device capable of generating and/or receiving ultrasound waves or ultrasound signals. As a nonlimiting example, ultrasound transducer may include one or more transmitters capable of converting electric signals into ultrasound waves. As another nonlimiting example, ultrasound transducer may include one or more receivers capable of converting ultrasound waves into electrical signals. Additionally, and/or alternatively, as another nonlimiting example, ultrasound transducer may include one or more transceivers capable of both transmitting and receiving ultrasound waves. "Ultrasound transducer" and "ultrasound probe" may be used interchangeably throughout this disclosure.

With continued reference to FIG. 1A, in one or more embodiments, input data and/or at least a medical image 110 may include ultrasound data. Ultrasound data may pertain to the heart and include one or more echocardiograms. Alternatively, ultrasound data may pertain to other tissues or organs and include data such as without limitation abdominal ultrasound data, among others. For the purposes of this disclosure, an "echocardiogram" is an ultrasound image specifically pertaining to the heart of a subject and generated using ultrasonic imaging system, as described above. Accordingly, the imaging technique used to collect echocardiograms may be called "echocardiography". Exemplary types of echocardiography may include intracardiac echocardiography (ICE), point-of-care ultrasound (POCUS), transthoracic echocardiography (TTE), transesophageal echocardiography (TEE), stress echocardiography, and intravascular ultrasound, among others. For the purposes of this disclosure, "abdominal ultrasound" is a diagnostic medical procedure utilizing high-frequency sound waves to produce visual images of the organs and structures within the abdominal cavity. This non-invasive technique may involve placing a transducer on the patient's abdomen, which emits sound waves that reflect off internal organs, creating real-time images displayed on a monitor. The procedure may be used to evaluate and diagnose conditions related to the liver, gallbladder, pancreas, kidneys, spleen, and blood vessels, providing essential information for clinical assessment and treatment planning.

With continued reference to FIG. 1A, in some cases, an echocardiogram may include an intracardiac echocardiogram (ICE). For the purposes of this disclosure, an "intracardiac echocardiogram (ICE)" is a two-dimensional (2D) ultrasound image collected by inserting, using a catheter, an ultrasound transducer inside the heart. It represents the anatomy (i.e., walls, chambers, blood vessels, etc.) of at least part of the heart. In some cases, ICE may be collected by crossing the interatrial septum with a transseptal puncture to permit catheter access from the right atrium to the left atrium; alternatively, a catheter may access the left heart by retrograding through the aorta and passing the aortic valve to enter the left ventricle. For the purposes of this disclosure, a "catheter" is a medical device including a thin, flexible tube made from medical-grade materials that may be inserted into part of a patient's body. Given its reduced size and flexible, noninvasive nature, a catheter may be configured to perform various functions such as collecting or transferring a clinical sample, administering a medicine or nutrient, providing a treatment for a disease, or performing a surgical procedure. Catheters are often manufactured for specific applications, such as cardiovascular, urological, gastrointestinal, neurovascular, and ophthalmic procedures.

With continued reference to FIG. 1A, in some cases, an echocardiogram may include a point-of-care ultrasound (POCUS). For the purposes of this disclosure, a "point-of-care ultrasound (POCUS)" is an ultrasound image collected using a medical technique that involves a portable, user-operated diagnostic imaging device and enables healthcare providers to perform real-time ultrasound examinations at the patient's bedside or in remote settings, without the need for specialized radiology departments. POCUS allows for immediate visualization of internal structures and organs, facilitating rapid diagnosis, treatment decisions, and monitoring of various medical conditions. POCUS devices typically feature compact designs, integrated transducers, and user-friendly interfaces, enabling non-radiologist clinicians to obtain high-quality images. Applications of POCUS may include, but are not limited to, assessing cardiac function, detecting fluid collections, guiding needle placements, and evaluating trauma patients. The portability and case of use of POCUS devices may significantly enhance clinical workflow, improve patient outcomes, and expand access to diagnostic imaging in diverse healthcare environments.

With continued reference to FIG. 1A, in some cases, an echocardiogram may include a transthoracic echocardiogram (TTE). For the purposes of this disclosure, a "transthoracic echocardiogram (TTE)" is a 2D ultrasound image of the heart collected by placing an ultrasound probe or ultrasound transducer on a patient's chest or abdomen to collect various views of the heart. In some cases, an echocardiogram may include a transesophageal echocardiogram (TEE). For the purposes of this disclosure, a "transesophageal echocardiogram (TEE)" is a 2D ultrasound image of the heart collected by passing a specialized probe or catheter containing an ultrasound transducer at its tip into a patient's esophagus. In some cases, an echocardiogram may include a stress cardiogram. For the purposes of this disclosure, a "stress echocardiogram" is a diagnostic medical procedure that assesses cardiac function by utilizing ultrasound imaging to visualize the heart's activity under induced physical stress. This procedure involves obtaining echocardiographic images of the heart at rest, followed by images captured during or immediately after physical exercise, or pharmacologically induced stress if the patient is unable to exercise. Stress echocardiogram may be used to evaluate myocardial performance, detect ischemia (i.e., a case of restricted or reduced blood flow in part of a body), and identify areas of compromised blood flow, providing critical information for diagnosing and managing various cardiac conditions.

With continued reference to FIG. 1A, for the purposes of this disclosure, a "subject" or "patient" is a human or any individual organism, on whom or on which a procedure, study, or otherwise experiment, may be conducted. As nonlimiting examples, patient may include human patient with symptoms of atrial or ventricular fibrillation and/or undergoing cardiac ablation, an individual undergoing cardiac screening, a participant in a clinical trial, an individual with congenital heart disease, a heart transplant candidate, an individual receiving follow-up care after cardiac surgery, a healthy volunteer, an individual with heart failure, or the like. Additionally, and/or alternatively, patient may include a pet or an animal model (i.e., an animal used to model certain medical conditions such as a laboratory rat). "Subject", "patient", and "entity" may be used interchangeably throughout this disclosure.

With continued reference to FIG. 1A, processor 102 is configured to generate an electro-anatomical mapping 122 as a function of input data 106. For the purposes of this disclosure, an "electro-anatomical mapping" or "electro-anatomical map" is a sophisticated diagnostic tool that merges electrical activity data with anatomical imaging to create a detailed, 3D representation of a conduction system pertaining to a tissue or organ. Electro-anatomical mapping is typically generated by inserting a catheter with electrodes into the heart to record electrical signals and integrating these electrical signals with anatomical imaging using specialized mapping software. This results in a detailed, three-dimensional representation of the heart's electrical conduction system, which may be crucial for diagnosing and treating cardiac arrhythmias. An electro-anatomical mapping may be used to accurately diagnose and treat cardiac arrhythmias by providing clinicians with precise information about the heart's electrical pathways and structural features.

With continued reference to FIG. 1A, in one or more embodiments, one or more machine learning models may be used to perform certain function or functions of apparatus 100, such as generation of electro-anatomical mapping 122, as described below. Processor 102 may use a machine learning module to implement one or more algorithms as described herein or generate one or more machine learning models, as described below. However, machine learning module is exemplary and may not be necessary to generate one or more machine learning models and perform any machine learning described herein. In one or more embodiments, one or more machine learning models may be generated using training data. Training data may include inputs and corresponding predetermined outputs so that machine learning model may use correlations between the provided exemplary inputs and outputs to develop an algorithm and/or relationship that then allows the machine learning model to determine its own outputs for inputs. Training data may contain correlations that a machine learning process may use to model relationships between two or more categories of data elements. Exemplary inputs and outputs may be retrieved from a database, selected from one or more EHRs, or be provided by a user. In one or more embodiments, machine learning module may obtain training data by querying a communicatively connected database that includes past inputs and outputs. Training data may include inputs from various types of databases, resources, and/or user inputs and outputs correlated to each of those inputs, so that machine learning model may determine an output. Correlations may indicate causative and/or predictive links between data, which may be modeled as relationships, such as mathematical relationships, by machine learning models, as described in further detail below. In one or more embodiments, training data may be formatted and/or organized by categories of data elements by, for example, associating data elements with one or more descriptors corresponding to categories of data elements. As a nonlimiting example, training data may include data entered in standardized forms by persons or processes, such that entry of a given data element in a given field in a form may be mapped to one or more descriptors of categories. Elements in training data may be linked to descriptors of categories by tags, tokens, or other data elements. In one or more embodiments, training data may include previous outputs such that one or more machine learning models may iteratively produce outputs.

With continued reference to FIG. 1A, processor 102 is configured to generate electro-anatomical mapping 122 using at least a machine learning model 124. At least a machine learning model 124 is trained using electro-anatomical mapping training data 126. Electro-anatomical mapping training data 126 include exemplary medical images and exemplary electrograms as input correlated to exemplary electro-anatomical mappings as output. In one or more embodiments, exemplary medical images may include historical medical images pertaining to a plurality of entities and collected prior to one or more historical medical procedures (i.e., pre-procedural medical images). In some cases, historical medical images may include historical CT scans, historical MRI scans, historical ultrasound data, and/or the like. In one or more embodiments, exemplary electrograms may include historical electrograms pertaining to plurality of entities, wherein the historical electrograms are collected prior to one or more historical medical procedures (i.e., pre-procedural electrograms) and temporally correlated with exemplary medical images. In some cases, historical electrograms may include historical ECGs, EEGs, or the like. In one or more embodiments, exemplary electro-anatomical mappings may include historical electro-anatomical mappings pertaining to a plurality of patients or entities and collected during one or more historical medical procedures (i.e., procedural electro-anatomical mappings). In some cases, historical electro-anatomical mappings may include historical cardiac electro-anatomical mappings pertaining to one or more ablation procedures. In some cases, historical medical images, historical electrograms, and/or historical electro-anatomical mappings may be correlated with the same patient or group of patients. In some cases, historical medical images, historical electrograms, and/or historical electro-anatomical mappings may be collected within a certain time window before their respective medical procedures. As a nonlimiting example, this time window may be 1, 2, 3, 4, 5, 6, 7, 8, 9, 10, 11, or 12 months before a scheduled medical procedure. Implementation of at least a machine learning model may be consistent with any type of machine learning model or algorithm described in this disclosure. In one or more embodiments, electro-anatomical mapping training data 126 may include data specifically synthesized for training purposes using one or more generative models. As a nonlimiting example, electro-anatomical mapping training data 126 may be extracted from medical literature. In one or more embodiments, one or more historic queries may be incorporated into electro-anatomical mapping training data 126 upon validation. In one or more embodiments, electro-anatomical mapping training data 126 may be retrieved from one or more databases, EHRs, and/or other repositories of similar nature, or be supplied as one or more user inputs. In one or more embodiments, at least a portion of electro-anatomical mapping training data 126 may be added, deleted, replaced, or otherwise updated as a function of one or more inputs from one or more users.

With continued reference to FIG. 1A, apparatus 100 may be used to provide clinical decision support for an ablation procedure 128. For the purposes of this disclosure, an "ablation procedure" or "cardiac ablation procedure" is a procedure used for treatment of irregular heartbeats (i.e., arrhythmias). It often uses heat or cold to create tiny scars in the heart that block faulty heart signals and help restore a healthy heartbeat. Ablation procedures that use heat are termed radiofrequency (RF) ablations or rhizotomies, whereas ablation procedures that use cold are termed cryo-ablations instead. In some cases, an ablation procedure may include a pulse field ablation procedure, which is a relatively new ablation procedure that induces programed cell death (i.e., apoptosis). In some cases, an ablation procedure may include a plurality of dosage parameters. Ablation procedure is most often done using catheters that are inserted through a blood vessel. Typical cases of arrhythmias that may potentially be treated using ablation procedures include atrial fibrillation, ventricular fibrillation, atrial flutter, and Wolff-Parkinson-White syndrome, among others. For the purposes of this disclosure, "atrial fibrillation" is a medical condition of an irregular (and often very rapid) heart rhythm in the upper chambers of the heart (i.e., the two atria). As a result, blood doesn't flow as well as it should from the atria to the lower chambers of the heart (i.e., the two ventricles). Atrial fibrillation may lead to blood clots in the heart and may increase the risk of stroke, heart failure, and other heart-related complications. Atrial fibrillation may be contrasted to ventricular fibrillation, wherein it is the lower heart chambers (i.e., the two ventricles) of the heart that contract in a very rapid and uncoordinated manner instead; as a result, the heart doesn't pump blood efficiently to the rest of the body.

With continued reference to FIG. 1A, in one or more embodiments, generating electro-anatomical mapping 122 may include generating a putative electro-anatomical mapping 122. For the purposes of this disclosure, a "putative electro-anatomical mapping" is a tentative electro-anatomical mapping 122 proposed by apparatus 100 and requires further validation 130. For the purposes of this disclosure, "validation" is a process of confirming whether hypothesis is correct or not based on an independent information source. Validation may be either automated or manual. In one or more embodiments, results of validation may be binary, i.e., "correct" vs. "incorrect". In one or more embodiments, results of validation may be expressed on one or more continuous scales. As a nonlimiting example, results of validation may include one or more confidence scores, e.g., a 95/100 or a 5/5. Accordingly, processor 102 may be configured to validate putative electro-anatomical mapping 122 using a plurality of quality assurance (QS) parameters 132. For the purposes of this disclosure, a "quality assurance (QS) parameter" is a specific criterion or standard used to evaluate the quality and performance of a system, process, or product. These parameters are essential for ensuring that a system, process, or product meets predefined requirements and user expectations. QS parameters may encompass a range of attributes, including without limitation functionality, reliability, usability, efficiency, maintainability, and portability, among others. QS parameters may be measured through various testing methods, such as unit tests, integration tests, and performance tests, among others, to identify and address defects, enhance quality, and ensure compliance with industry standards. Processor 102 may then be further configured to create electro-anatomical mapping 122 by fine-tuning putative electro-anatomical mapping 122 as a function of an outcome of validation 130.

With continued reference to FIG. 1A, in one or more embodiments, electro-anatomical mapping 122 may include a color-coded heat map 134. For the purposes of this disclosure, a "color-coded heat map" is a visual representation that uses a plurality of different colors to indicate the value of a variable across a plurality of spatial regions. In some cases, a first region of electro-anatomical mapping 122 may be associated with a first electrical activity, such as a first electrical potential, and a second region of the electro-anatomical mapping 122 may be associated with a second electrical activity different from the first electrical activity, such as a second electrical potential different from the first electrical potential; accordingly, the first region may be highlighted with a first color, and the second region may be highlighted with a second color different from the first color. As a nonlimiting example, a first color may be red to indicate a positive electrical potential, whereas a second color may be blue to indicate a negative electrical potential. In some cases, a continuum containing a plurality of colors, such as a spectrum that varies from red to purple, may be used across a plurality of regions without sharp transition in between.

With continued reference to FIG. 1A, in one or more embodiments, apparatus 100 may include or be communicatively connected to a display device 136. For the purposes of this disclosure, a "display device" is a device configured to show visual information. In some cases, a display device may include a liquid crystal display (LCD), a cathode ray tube (CRT), a plasma display, a light emitting diode (LED) display, and any combinations thereof. A display device may include, but is not limited to, a smartphone, tablet, laptop, monitor, tablet, and the like. A display device may include a separate device that includes a transparent screen configured to display computer-generated images and/or information. In one or more embodiments, a display device may be configured to visually present data through a user interface or a graphical user interface (GUI) to at least a user, wherein the user may interact with the data through the user interface or GUI, as described below. In one or more embodiments, a user may view GUI through a display device. In one or more embodiments, a display device may be located on remote device, as described below. In one or more embodiments, a display device and imaging device 108 may be the same device or integrated within the same device, such as a laptop, a smartphone or a tablet. Additional details will be provided below in this disclosure through nonlimiting examples.

With continued reference to FIG. 1A, display device 136 may include a remote device. For the purposes of this disclosure, a "remote device" is a computer device separate and distinct from apparatus 100. For example, and without limitation, a remote device may include a smartphone, a tablet, a laptop, a desktop computer, or the like. In one or more embodiments, a remote device may be communicatively connected to apparatus 100 such as, for example, through network communication, through Bluetooth communication, and/or the like. In one or more embodiments, processor 102 may receive input data 106 and/or initiate one or more of subsequent steps through a remote device. In one or more embodiments, one or more inputs from one or more users may be submitted through a user interface, such as a GUI, displayed using a remote device, as described below.

With continued reference to FIG. 1A, apparatus 100 includes or is communicatively connected to a user interface 138. Accordingly, processor 102 is configured to display electro-anatomical mapping 122 using user interface 138. For the purposes of this disclosure, a "user interface" is a means by which a user and a computer system interact, for example, using input devices and software. User interface may include a graphical user interface (GUI), command line interface (CLI), menu-driven user interface, touch user interface, voice user interface (VUI), form-based user interface, any combination thereof, or the like. In one or more embodiments, a user may interact with a user interface using computing device distinct from and communicatively connected to processor 102, such as a smartphone, tablet, or the like operated by the user. A user interface may include one or more graphical locator and/or cursor facilities allowing user to interact with graphical models and/or combinations thereof, for instance using a touchscreen, touchpad, mouse, keyboard, and/or other manual data entry device. For the purposes of this disclosure, a "graphical user interface (GUI)" is a type of user interface that allows end users to interact with electronic devices through visual representations. In one or more embodiments, a GUI may include icons, menus, other visual indicators or representations (graphics), audio indicators such as primary notation, display information, and related user controls. A menu may contain a list of choices and may allow users to select one from them. A menu bar may be displayed horizontally across the screen as a pull-down menu. A menu may include a context menu that appears only when user performs a specific action. Files, programs, web pages, and the like may be represented using a small picture within a GUI. In one or more embodiments, a GUI may include a graphical visualization of a user profile and/or the like. In one or more embodiments, processor 102 may be configured to modify and/or update a GUI as a function of at least an input or the like by populating a user interface data structure and visually presenting data through modification of the GUI.

With continued reference to FIG. 1A, in one or more embodiments, a GUI may contain one or more interactive elements. For the purposes of this disclosure, an "interactive element" is an element within a GUI that allows for communication with processor 102 by one or more users. For example, and without limitation, interactive elements may include a plurality of tabs wherein selection of a particular tab, such as for example, by using a fingertip, may indicate to a system to perform a particular function and display the result through a GUI. In one or more embodiments, interactive element may include tabs within a GUI, wherein the selection of a particular tab may result in a particular function. In one or more embodiments, interactive elements may include words, phrases, illustrations, and the like to indicate a particular process that one or more users would like a system to perform. A person of ordinary skill in the art, upon reviewing the entirety of this disclosure, will be aware of various ways in which user interfaces, GUIs, and/or elements thereof may be implemented and/or used as described in this disclosure.

With continued reference to FIG. 1A, in one or more embodiments, display device 136 and/or remote device may be configured to display at least an event handler graphic corresponding to at least an event handler. For the purposes of this disclosure, an "event handler graphic" is a graphical element with which user interacts using display device 136 and/or remote device to enter data, for instance and without limitation, for input data 106 or the like as described above. An event handler graphic may include, without limitation, a button, a link, a checkbox, a text entry box and/or window, a drop-down list, a slider, or any other event handler graphic deemed suitable by a person of ordinary skill in the art upon reviewing the entirety of this disclosure. For the purposes of this disclosure, an "event handler" is a module, data structure, function, and/or routine that performs an action on display device 136 and/or remote device in response to one or more user inputs. For instance, and without limitation, an event handler may record data corresponding to user selections of previously populated fields such as drop-down lists and/or text auto-complete and/or default entries, data corresponding to user selections of checkboxes, radio buttons, or the like, potentially along with automatically entered data triggered by such selections, user entry of textual data using a keyboard, touchscreen, speech-to-text program, or the like. An event handler may generate prompts for further information, may compare data to validation rules such as requirements that the data in question be entered within certain numerical ranges, and/or may modify data and/or generate warnings to user in response to such requirements. An event handler may convert data into expected and/or desired formats, for instance such as date formats, currency entry formats, name formats, or the like. An event handler may transmit data from a remote device to computing device.

With continued reference to FIG. 1A, in one or more embodiments, an event handler may include a cross-session state variable. For the purposes of this disclosure, a "cross-session state variable" is a variable recording data entered on remote device during a previous session. Such data may include, for instance, previously entered text, previous selections of one or more elements as described above, or the like. For instance, a cross-session state variable data May represent a search that user entered in a past session. A cross-session state variable may be saved using any suitable combination of client-side data storage on remote device and server-side data storage on computing device; for instance, data may be saved wholly or in part as a "cookie" which may include data or an identification of remote device to prompt provision of the cross-session state variable by the computing device, which may store the data on the computing device. Alternatively, or additionally, computing device may use login credentials, device identifier, and/or device fingerprint data to retrieve cross-session state variable, which the computing device may transmit to a remote device. A Cross-session state variable may include at least a prior session datum. A prior session datum may include any element of data that may be stored in cross-session state variable. An event handler graphic may be further configured to display at least a prior session datum, for instance and without limitation, by auto-populating user query data from previous sessions.

With continued reference to FIG. 1A, in one or more embodiments, processor 102 and/or computing device may configure display device 136 and/or remote device to generate a graphical view. For the purposes of this disclosure, a "graphical view" is a data structure that results in display of one or more graphical elements on a screen. A graphical view may include at least a display element. For the purposes of this disclosure, a "display element" is an image that a program and/or data structure cause to be displayed. Display elements may include, without limitation, windows, pop-up boxes, web browser pages, display layers, and/or any other display element deemed relevant by a person of ordinary skill in the art upon reviewing the entirety of this disclosure. A graphical view may include at least a selectable event graphic corresponding to one or more selectable event handlers. For the purposes of this disclosure, a "selectable event graphic" is a graphical element that, upon selection, will trigger an action to be performed. Selection may be performed using a cursor or other locator as manipulated using a locator device such as a mouse, touchscreen, track pad, joystick, or the like. As a nonlimiting example, a selectable event graphic may include a redirection link, defined as a hyperlink, button, image, portion of an image, and/or other graphic containing or referring to a uniform resource locator (URL) and/or other resource locator to another graphical view including without limitation buttons, and/or to a process that performs navigation to such URL and/or other resource locator upon selection of selectable event graphic. Redirection may be performed using any event handler, including without limitation event handlers detecting the click of a mouse or other locator, access of redirection link using a touchscreen, the selection of any key, mouseover events, or the like.

With continued reference to FIG. 1A, in one or more embodiments, processor 102 may be further configured to identify at least a target location 140 pertaining to a medical procedure 142 within electro-anatomical mapping 122. For the purposes of this disclosure, a "target location" is a location within a tissue or an organ that is of medical interest. Such medical interest may be pertaining to one or more specific steps to perform in a medical procedure. In some cases, medical procedure 142 may include ablation procedure 128, consistent with details described above. In some cases, electro-anatomical mapping 122 may be used as an initial mapping for an ablation procedure. Accordingly, processor 102 may be configured to highlight at least a target location 140 within electro-anatomical mapping 122 using user interface 138, consistent with details described above.

With continued reference to FIG. 1A, in some cases, processor 102 may be configured to receive, from a navigation system 144, a location 146 of a catheter. For the purposes of this disclosure, a "navigation system" is a system that monitors an exact position and/or orientation or a medical device with respect to a tissue or an organ, thereby providing guidance regarding subsequent steps to be performed by the medical device. Accordingly, processor 102 may be configured to display, using user interface 138, location 146 of catheter on electro-anatomical mapping 122, consistent with details described above. In some cases, processor 102 may be further configured modify one or more aspects of electro-anatomical mapping 122 as a function of location 146 of the catheter. As a nonlimiting example, processor 102 may be configured to replace or update a first view with a second view different from the first view, in user interface 138, as a catheter translates, rotates, or otherwise moves from a first location/angle to a second location/angle different from the first location/angle, thereby providing real-time navigation. As another nonlimiting example, processor 102 may be configured to zoom in or zoom out at certain locations or regions within electro-anatomical mapping 122. As another nonlimiting example, processor 102 may be configured to correct one or more errors or inaccuracies within electro-anatomical mapping 122 using up-to-date information received by a catheter.

With continued reference to FIG. 1A, in one or more embodiments, processor 102 may be further configured to identify at least a medical feature 148 within electro-anatomical mapping 122. For the purposes of this disclosure, a "medical feature" is a structural or functional characteristic that describes one or more aspects regarding a patient's health. In some cases, a medical feature may include one or more specific anatomical traits relevant to the successful completion of a medical procedure. As nonlimiting examples, medical features may include a presence of thrombus in the left atrial appendage of the heart, a presence of calcification at a heart valve, a thickness including an abnormal thickness of a heart wall, an abnormal heart valve anatomy or function, among others. Medical features described herein may be consistent with any detail disclosed in disclosed in U.S. patent application Ser. No. 18/787,453, filed on Jul. 29, 2024, entitled "APPARATUS AND METHODS FOR IDENTIFICATION OF MEDICAL FEATURES IN A HEART", the entirety of which is incorporated herein by reference. Accordingly, in some cases, processor 102 may be configured to adjust at least a parameter 150 pertaining to medical procedure 142 as a function of at least a medical feature. For example, in the case of ablation procedure 128, adjustable parameters may include without limitation voltage, pulse duration, frequency, pulse width, amplitude, power of ablation, total energy delivered, total treatment time, energy delivered to a particular location, treatment time at a particular location, current, average power, peak power, and biphasic vs monophasic pulse delivery, among others. In some cases, processor 102 may be configured to alert a medical professional operating a catheter regarding one or more medical features that should be avoided.

With continued reference to FIG. 1A, in one or more embodiments, a computer vision module configured to perform one or more computer vision tasks such as, without limitation, object recognition, feature detection, edge/corner detection thresholding, or machine learning process may be used to recognize specific features or attributes. For the purposes of this disclosure, a "computer vision module" is a computational component designed to perform one or more computer vision, image processing, and/or modeling tasks. Computer vision module may include an image processing module, wherein images may be pre-processed using the image processing module. For the purposes of this disclosure, an "image processing module" is a component designed to process digital images such as images described herein. For example, and without limitation, image processing module may be configured to compile a plurality of images of a multi-layer scan to create an integrated image. In one or more embodiments, image processing module may include a plurality of software algorithms that can analyze, manipulate, or otherwise enhance an image, such as, without limitation, a plurality of image processing techniques as described below. In one or more embodiments, computer vision module may also include hardware components such as, without limitation, one or more graphics processing units (GPUs) that can accelerate the processing of a large number of images. In one or more embodiments, computer vision module may be implemented with one or more image processing libraries such as, without limitation, OpenCV, PIL/Pillow, ImageMagick, and the like. In a nonlimiting example, in order to generate one or more labels and/or recognize one or more reference attributes, one or more image processing tasks, such as noise reduction, contrast enhancement, intensity normalization, image segmentation, and/or the like, may be performed by computer vision module on a plurality of images to isolate certain features or components from the rest. In one or more embodiments, one or more machine learning models may be used to perform segmentations, for example, and without limitation, a U-net (i.e., a convolution neural network containing a contracting path as an encoder and an expansive path as a decoder, wherein the encoder and the decoder forms a U-shaped structure). A person of ordinary skill in the art, upon reviewing the entirety of this disclosure, will be aware of various image processing, computer vision, and modeling tasks that may be performed by processor 102.

With continued reference to FIG. 1A, in one or more embodiments, one or more functions of apparatus 100 may involve a use of image classifiers to classify images within any data described in this disclosure. For the purposes of this disclosure, an "image classifier" is a machine learning model that sorts inputs of image information into categories or bins of data, outputting the categories or bins of data and/or labels associated therewith. Image classifier may include a mathematical model, a neural net, or a program generated by a machine learning algorithm known as a "classification algorithm", as described in further detail below. Image classifier may be configured to output at least a datum that labels or otherwise identifies a set of images that are clustered together, found to be close under a distance metric as described below, or the like. Computing device and/or another device may generate image classifier using a classification algorithm. For the purposes of this disclosure, a classification algorithm is a process whereby computing device derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, Fisher's linear discriminant, quadratic classifiers, decision trees, boosted trees, random forest classifiers, learning vector quantization, and/or neural network-based classifiers. In one or more embodiments, processor 102 may use image classifier to identify a key image in any data described in this disclosure. For the purposes of this disclosure, a "key image" is an element of visual data used to identify and/or match elements to each other. In one or more embodiments, key image may include part of a medical image such as a CT scan, an MRI scan, or the like, with features that unambiguously identify the type of a medical image. Image classifier may be trained with binarized visual data that have already been classified to determine key images in any other data described in this disclosure. For the purposes of this disclosure, "binarized visual data" are visual data that are described in a binary format. For example, binarized visual data of a photo may comprise ones and zeroes, wherein the specific sequence of ones and zeros may be used to represent the photo. Binarized visual data may be used for image recognition wherein a specific sequence of ones and zeroes may indicate a product present in the image. An image classifier may be consistent with any classifier as discussed herein. An image classifier may receive input data (e.g., medical images 110) described in this disclosure and output a key image with the data. In one or more embodiments, image classifier may be used to compare visual data in one data set with visual data in another data set.

With continued reference to FIG. 1A, processor 102 may be configured to perform feature extraction on at least a medical image 110 or the like. For the purposes of this disclosure, "feature extraction" is a process of transforming an initial data set into informative measures and values. For example, feature extraction may include a process of determining one or more geometric features of an anatomic structure. In one or more embodiments, feature extraction may be used to determine one or more spatial relationships within a drawing that may be used to uniquely identify one or more features. In one or more embodiments, processor 102 may be configured to extract one or more regions of interest, wherein the regions of interest may be used to extract one or more features using one or more feature extraction techniques.

With continued reference to FIG. 1A, processor 102 may be configured to perform one or more of its functions, such as identification of at least a medical feature 148, using a feature learning algorithm. For the purposes of this disclosure, a "feature learning algorithm" is a machine learning algorithm that identifies associations between elements of data in a data set where particular outputs and/or inputs are not specified. Data set may include without limitation a training data set. For instance, and without limitation, a feature learning algorithm may detect co-occurrences of elements of data, as defined above, with each other. Computing device may perform feature learning algorithm by dividing elements or sets of data into various sub-combinations of such data to create new elements of data and evaluate which elements of data tend to co-occur with which other elements. In one or more embodiments, feature learning algorithm may perform clustering of data.

With continued reference to FIG. 1A, feature learning and/or clustering algorithm may be implemented, as a non-limiting example, using a k-means clustering algorithm. For the purposes of this disclosure, a "k-means clustering algorithm" is a type of cluster analysis that partitions n observations or unclassified cluster data entries into k clusters in which each observation or unclassified cluster data entry belongs to the cluster with the nearest mean. For the purposes of this disclosure, "cluster analysis" is a process that includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering, whereby each observation or unclassified cluster data entry belongs to a cluster or not. Cluster analysis may include soft clustering or fuzzy clustering, whereby each observation or unclassified cluster data entry belongs to each cluster to a certain degree such as for example a likelihood of belonging to a cluster; for instance, and without limitation, a fuzzy clustering algorithm may be used to identify clustering of elements of a first type or category with elements of a second type or category, and vice versa, as described below. Cluster analysis may include strict partitioning clustering, whereby each observation or unclassified cluster data entry belongs to exactly one cluster. Cluster analysis may include strict partitioning clustering with outliers, whereby observations or unclassified cluster data entries may belong to no cluster and may be considered outliers. Cluster analysis may include overlapping clustering whereby observations or unclassified cluster data entries may belong to more than one cluster. Cluster analysis May include hierarchical clustering, whereby observations or unclassified cluster data entries that belong to a child cluster also belong to a parent cluster.

With continued reference to FIG. 1A, computing device may generate a k-means clustering algorithm by receiving unclassified data and outputting a definite number of classified data entry clusters, wherein the data entry clusters each contain cluster data entries. K-means algorithm may select a specific number of groups or clusters to output, identified by a variable "k". Generating k-means clustering algorithm includes assigning inputs containing unclassified data to a "k-group" or "k-cluster" based on feature similarity. Centroids of k-groups or k-clusters may be utilized to generate classified data entry cluster. K-means clustering algorithm may select and/or be provided "k" variable by calculating k-means clustering algorithm for a range of k values and comparing results. K-means clustering algorithm may compare results across different values of k as the mean distance between cluster data entries and cluster centroid. K-means clustering algorithm may calculate mean distance to a centroid as a function of k value, and the location of where the rate of decrease starts to sharply shift, which may be utilized to select a k value. Centroids of k-groups or k-cluster include a collection of feature values which are utilized to classify data entry clusters containing cluster data entries. K-means clustering algorithm may act to identify clusters of closely related data, which may be provided with user cohort labels; this may, for instance, generate an initial set of user cohort labels from an initial set of data, and may also, upon subsequent iterations, identify new clusters to be provided new labels, to which additional data may be classified, or to which previously used data may be reclassified.

With continued reference to FIG. 1A, generating a k-means clustering algorithm may include generating initial estimates for k centroids which may be randomly generated or randomly selected from unclassified data input. K centroids may be utilized to define one or more clusters. K-means clustering algorithm may assign unclassified data to one or more k-centroids based on the squared Euclidean distance by first performing a data assigned step of unclassified data. K-means clustering algorithm may assign unclassified data to its nearest centroid based on the collection of centroids ci of centroids in set C. Unclassified data may be assigned to a cluster based on $\mathrm{argmin}_{ci \ni C} \mathrm{dist}(c_i, x)^2$, where argmin includes argument of the minimum, ci includes a collection of centroids in a set C, and dist includes standard Euclidean distance. K-means clustering module may then recompute centroids by taking a mean of all cluster data entries assigned to a centroid's cluster. This may be calculated based on $c_i = 1/|S_i| \Sigma x_i \ni S_i^{xi}$. K-means clustering algorithm may continue to repeat these calculations until a stopping criterion has been satisfied such as when cluster data entries do not change clusters, the sum of the distances have been minimized, and/or some maximum number of iterations has been reached.

With continued reference to FIG. 1A, k-means clustering algorithm may be configured to calculate a degree of similarity index value. For the purposes of this disclosure, a "degree of similarity index value" is a distance measured between each data entry cluster generated by k-means clustering algorithm and a selected element. Degree of similarity index value may indicate how close a particular combination of elements is to being classified by k-means algorithm to a particular cluster. K-means clustering algorithm may evaluate the distances of the combination of elements to the k-number of clusters output by k-means clustering algorithm. Short distances between an element of data and a cluster may indicate a higher degree of similarity between the element of data and a particular cluster. Longer distances between an element and a cluster may indicate a lower degree of similarity between the element to be compared and/or clustered and a particular cluster.

With continued reference to FIG. 1A, k-means clustering algorithm selects a classified data entry cluster as a function of the degree of similarity index value. In one or more embodiments, k-means clustering algorithm may select a classified data entry cluster with the smallest degree of similarity index value indicating a high degree of similarity between an element and the data entry cluster. Alternatively, or additionally, k-means clustering algorithm may select a plurality of clusters having low degree of similarity index values to elements to be compared and/or clustered thereto, indicative of greater degrees of similarity. Degree of similarity index values may be compared to a threshold number indicating a minimal degree of relatedness suitable for inclusion of a set of element data in a cluster, where degree of similarity indices a-n falling under the threshold number may be included as indicative of high degrees of relatedness. The above-described illustration of feature learning using k-means clustering is included for illustrative purposes only and should not be construed as limiting potential implementation of feature learning algorithms; a person of ordinary skills in the art, upon reviewing the entirety of this disclosure, will be aware of various additional or alternative feature learning approaches, such as particle swarm optimization (PSO) and generative adversarial network (GAN) that may be used consistently with this disclosure.

With continued reference to FIG. 1A, in one or more embodiments, processor 102 may use an image recognition algorithm to determine patterns within an image. In one or more embodiments, image recognition algorithm may include an edge-detection algorithm, which may detect one or more shapes defined by edges. For the purposes of this disclosure, an "edge detection algorithm" is or includes a mathematical method that identifies points in a digital image at which the image brightness changes sharply and/or has discontinuities. In one or more embodiments, such points may be organized into straight and/or curved line segments, which may be referred to as "edges". Edge detection may be performed using any suitable edge detection algorithm, including without limitation Canny edge detection, Sobel operator edge detection, Prewitt operator edge detection, Laplacian operator edge detection, and/or differential edge detection. Edge detection may include phase congruency-based edge detection, which finds all locations of an image where all sinusoids in the frequency domain, for instance when generated using a Fourier decomposition, may have matching phases which may indicate a location of an edge.

With continued reference to FIG. 1A, it should be noted that apparatus 100 and methods described herein are not limited to medical or cardiac applications only. For example, and without limitation, visualization capabilities disclosed herein may be effectively adapted for use within other organs, such as brain, where precision and minimally invasive diagnostics are also crucial. A person of ordinary skill in the art, upon reviewing the entirety of this disclosure, will recognize one or more embodiments described herein (although principally focused on the heart) and their underlaying principles may be readily transferrable to a broader spectrum of medical imaging and intervention applications such as, without limitation, transcatheter intervention (which is rapidly supplanting traditional open surgery), or other nonmedical contexts that are not currently disclosed.

Figure 1B:
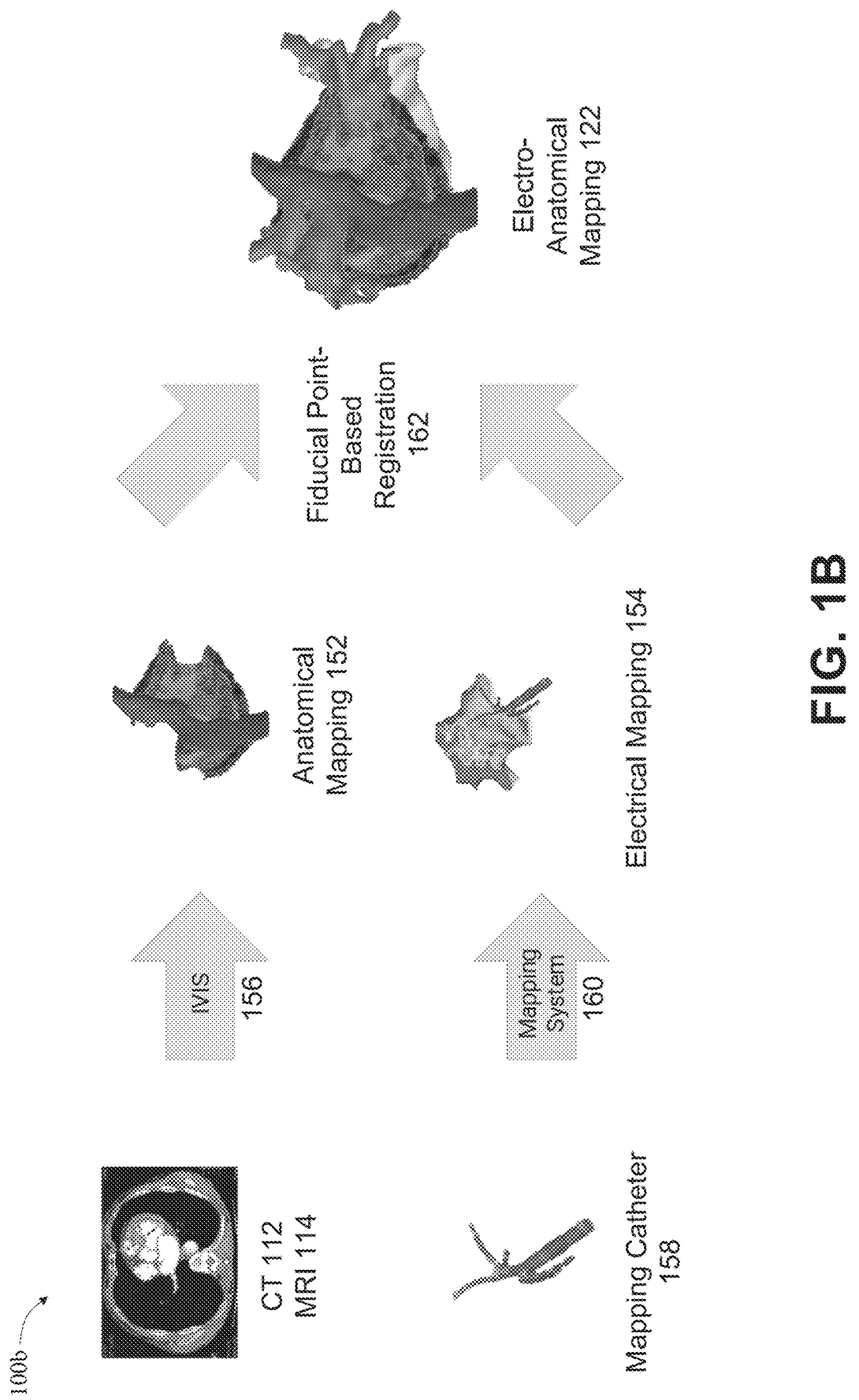
FIG. 1B is an exemplary embodiment of a workflow of the apparatus in FIG. 1A.

Referring now to FIG. 1B, an exemplary embodiment of a workflow 100b for apparatus 100 is illustrated. In one or more embodiments, generating electro-anatomical mapping 122 may involve a stepwise approach. Specifically, generating electro-anatomical mapping 122 may include generating an anatomical mapping 152 and an electrical mapping 154. For the purposes of this disclosure, an "anatomical mapping" is a mapping of anatomical structure of a tissue or an organ. In some cases, anatomical mapping 152 may be generated using an in vivo imaging system (IVIS) 156. Generation of anatomical mapping 152 may be consistent with details disclosed in U.S. patent application Ser. No. 18/376,688, filed on Oct. 4, 2023, entitled "APPARATUS AND METHODS FOR GENERATING A THREE-DIMENSIONAL (3D) MODEL OF CARDIAC ANATOMY VIA MACHINE-LEARNING", and U.S. patent application Ser. No. 18/426,604, filed on Oct. 4, 2023, entitled "APPARATUS AND METHOD FOR GENERATING A THREE-DIMENSIONAL (3D) MODEL OF CARDIAC ANATOMY BASED ON MODEL UNCERTAINTY", the entirety of each of which is incorporated herein by reference. For the purposes of this disclosure, an "electrical mapping" is a mapping of electrical activity of a tissue or an organ. Electrical mapping 154 may be generated using any suitable means recognized by a person of ordinary skill in the art upon reviewing the entirety of this disclosure, such as without limitation using a mapping catheter 158 and/or a mapping system 160.

With continued reference to FIG. 1B, in one or more embodiments, generating electro-anatomical mapping 122 may include aligning electrical mapping 154 with anatomical mapping 152 using fiducial point-based registration 162. For the purposes of this disclosure, "fiducial point-based registration" is a method used in image processing and computer vision to align or map two or more data sets into a common coordinate system. This technique may involve selecting distinct and easily identifiable points, known as fiducial points, in each data set. These points may serve as references or landmarks. By applying mathematical transformations, such as scaling, rotation, and translation, among others, datasets may be adjusted so that their corresponding fiducial points overlap as closely as possible. This process may be crucial in applications such as medical imaging, where accurate alignment of images is necessary for diagnosis and treatment planning.

Figure 2:
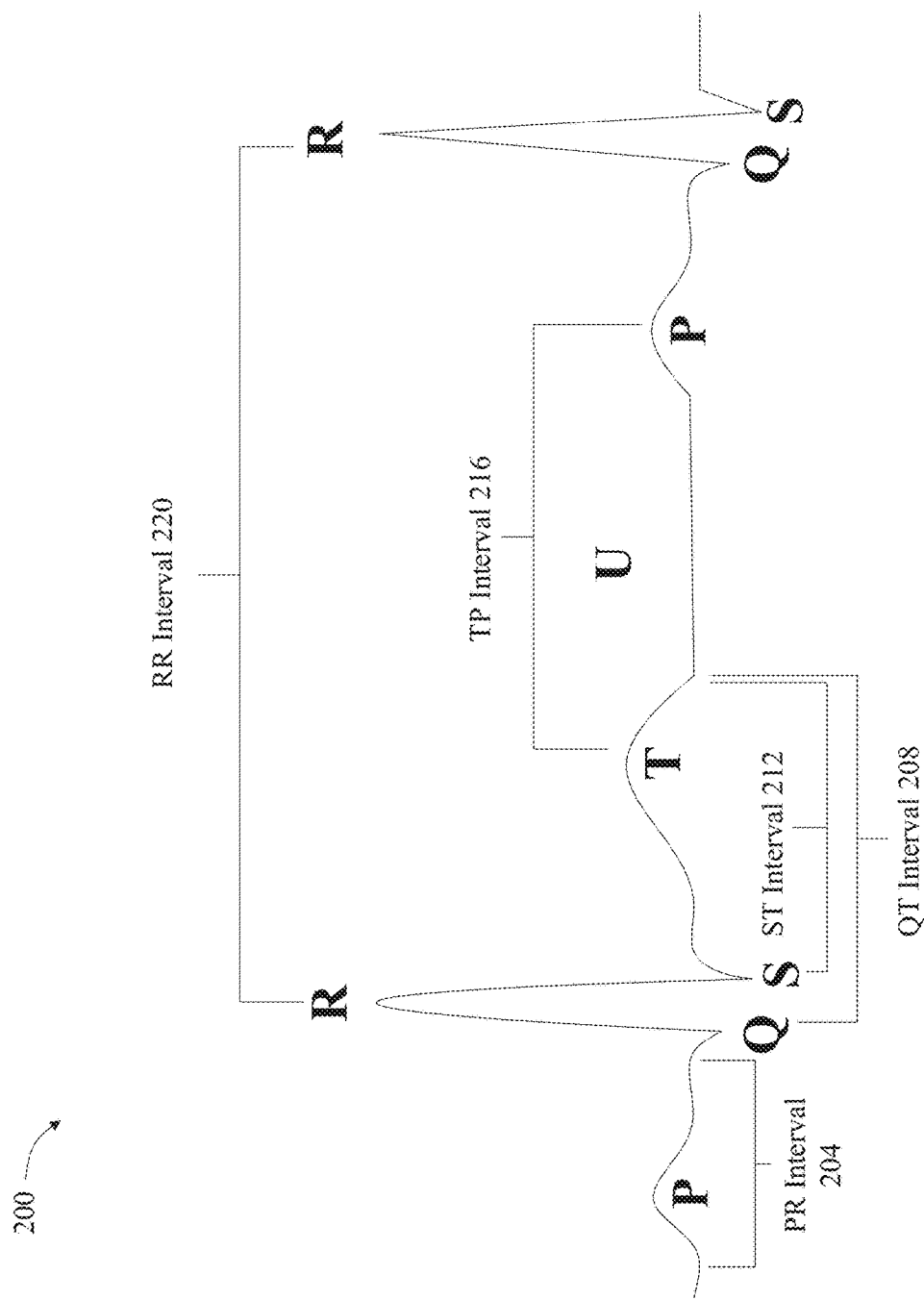
FIG. 2 is an illustration of an exemplary embodiment of an electrocardiogram (ECG)

Referring now to FIG. 2, in one or more embodiments, an exemplary embodiment 200 of an electrocardiogram (ECG) is illustrated. ECG may include a plurality of features such as P-wave, Q-wave, R-wave, S-wave, QRS complex, and T wave, as well as a plurality of parameters such a PR interval 204, QT interval 208, ST interval 212, TP interval 216, RR interval 220, and the like. P-wave may reflect atrial depolarization (activation). For the purposes of this disclosure, a "PR interval" is the distance between the onset of P-wave to the onset of QRS complex. PR interval 204 may be assessed to determine whether impulse conduction from the atria to the ventricles is normal. PR interval 204 may be measured in seconds. For the purposes of this disclosure, a "QT interval" is a reflection of the total duration of ventricular depolarization and repolarization and is measured from the onset of QRS complex to the end of T-wave. The QT duration may be inversely related to heart rate; i.e., QT interval 208 may increase at slower heart rates and decrease at higher heart rates. Therefore, to determine whether QT interval 208 is within normal limits, it may be necessary to adjust for the heart rate. A heart rate-adjusted QT interval 208 is referred to as a corrected QT interval 208 (QTc interval). A long QTc interval may indicate an increased risk of ventricular arrhythmias. The QTc interval may be in the range of 0.36 to 0.44 seconds. For the purposes of this disclosure, an "RR interval" is the time between two consecutive R waves. For the purposes of this disclosure, a "QRS complex" is a representation of the depolarization (activation) of ventricles depicted between Q-, R- and S-waves, although it may not always display all three waves. Since the electrical vector generated by the left ventricle is usually many times larger than the vector generated by the right ventricle, QRS complex is a reflection of left ventricular depolarization.

With continued reference to FIG. 2, for the purposes of this disclosure, an "ST interval" is the segment of ECG that starts at the end of QRS complex and extends to the beginning of T wave; it represents the early part of ventricular repolarization. ST segment may be relatively isoelectric, meaning it is at the baseline, with minimal elevation or depression. The normal duration of ST interval 212 is usually around 0.12 seconds. For the purposes of this disclosure, a "TP interval" is the segment of ECG that extends from the end of T wave to the beginning of the next P wave; it represents the time when the ventricles are fully repolarized and are in a resting state. The duration of TP interval 216 may vary but is typically short, as it may represent the brief pause between cardiac cycles. Significant deviations may be associated with certain conditions affecting repolarization. For the purposes of this disclosure, an "RR interval" is the time between two consecutive R waves of ECG; it may represent the duration of one cardiac cycle, encompassing both atrial and ventricular depolarization and repolarization. RR interval 220 may be measured in seconds and can be used to calculate heart rate (beats per minute) using $$\text{heart rate} = \frac{60}{RR \text{ Interval}}$$

(in seconds). The intervals described above may be used to determine a ventricular rate, i.e., the number of ventricular contractions (heartbeats) that occur in one minute, which may be closely related to RR interval 220 of ECG, as the RR interval 220 represents the time between two consecutive ventricular contractions.

Figure 3:
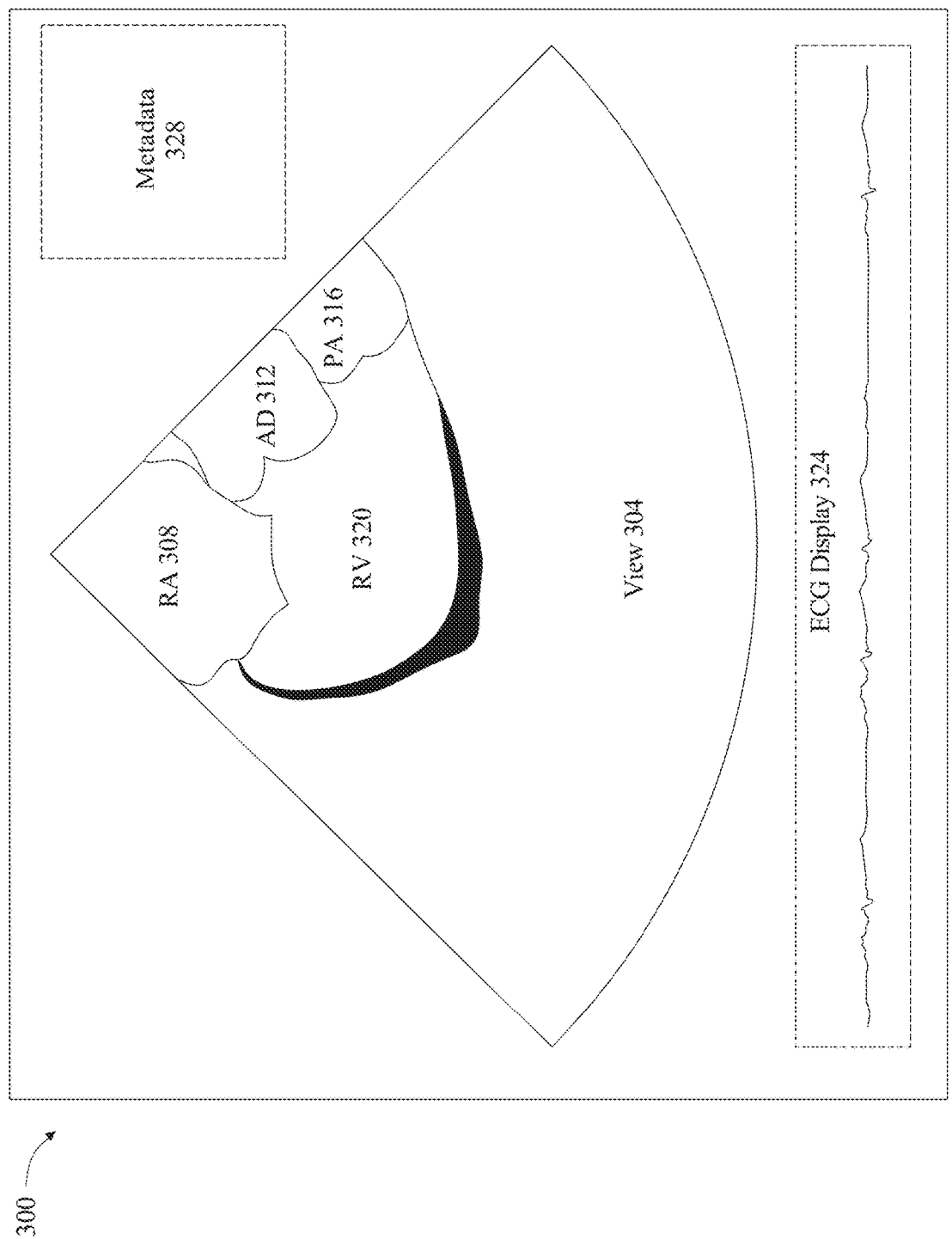
FIG. 3 is an illustration of an exemplary embodiment of an intracardiac echocardiogram (ICE)

Referring now to FIG. 3, an exemplary embodiment of an intracardiac echocardiogram (ICE) 300 is illustrated. As described above, input data 106 and/or at least a medical image 110 may include ultrasound data, such as without limitation an ICE 300. In one or more embodiments, ICE 300 may provide a real-time, dynamic a view 304 of the heart's interior structures, including, without limitation, right atrium (RA) 308, anterior descending (AD) 312, pulmonary atresia (PA) 316, and right ventricular (RV) 320.

With continued reference to FIG. 3, in one or more embodiments, ICE 300 may include a grayscale image. It should be noted that, in one or more embodiments, ICE 300 may be configured to visualize blood flow and/or blood flow patterns within heart via color doppler. In one or more embodiments, resolution and/or clarity of ICE 300 may be superior to transthoracic or transesophageal echocardiography due to that ICE catheter may be positioned inside heart, closer to the structures being imaged.

With continued reference to FIG. 3, in a nonlimiting example, heart chambers may appear as dark, anechoic (black) areas since they are filled with blood, which doesn't reflect ultrasound waves well. Heart walls, valves, and/or other structures may appear as varying shades of gray, depending on their density and composition. In one or more embodiments, color doppler overlays may show blood flow in different colors, indicating the direction and speed of blood flow. For instance, and without limitation, red may indicate flow towards the probe, whereas blue may indicate flow away from the probe.

With continued reference to FIG. 3, in one or more embodiments, ICE 300 may be synchronized with ECG data as described above, allowing for precise timing of cardiac events with anatomical visualization provided by ICE 300. In one or more embodiments, ICE 300 may include an ECG display 324 configured to display ECG waveform as a continuous line graph at the top, bottom, or side of the ICE 300. In one or more embodiments, specific parts of the cardiac cycle, e.g., systole or diastole, may be correlated and/or synchronized with visual data from ICE 300.

With continued reference to FIG. 3, additionally or alternatively, ICE 300 may be accompanied by metadata 328 displayed on the side or corners of ICE 300 as described herein. In one or more embodiments, metadata 328 may provide essential contextual information about ICE 300 and/or the corresponding patient. In a nonlimiting example, metadata 328 may include patient information (e.g., patient ID, name, DOB, age, gender, and the like), image acquisition details (e.g., date and time, probe type, frequency, depth, gain, and the like), procedure-related information (e.g., procedure name, operator, location, and the like), ECG trace, measurement annotations (e.g., any measurements taken directly on the image e.g., diameter, a value of thickness of a heart wall, and the like), image sequence information (e.g., image number, total number of frames, and the like), comments or notes, hospital or clinic information, and/or the like. A person of ordinary skill in the art, upon reviewing the entirety of this disclosure, will be aware of how ICE 300 and various components thereof may be incorporated within apparatus 100 to generate electro-anatomical mapping 122.

Figure 4:
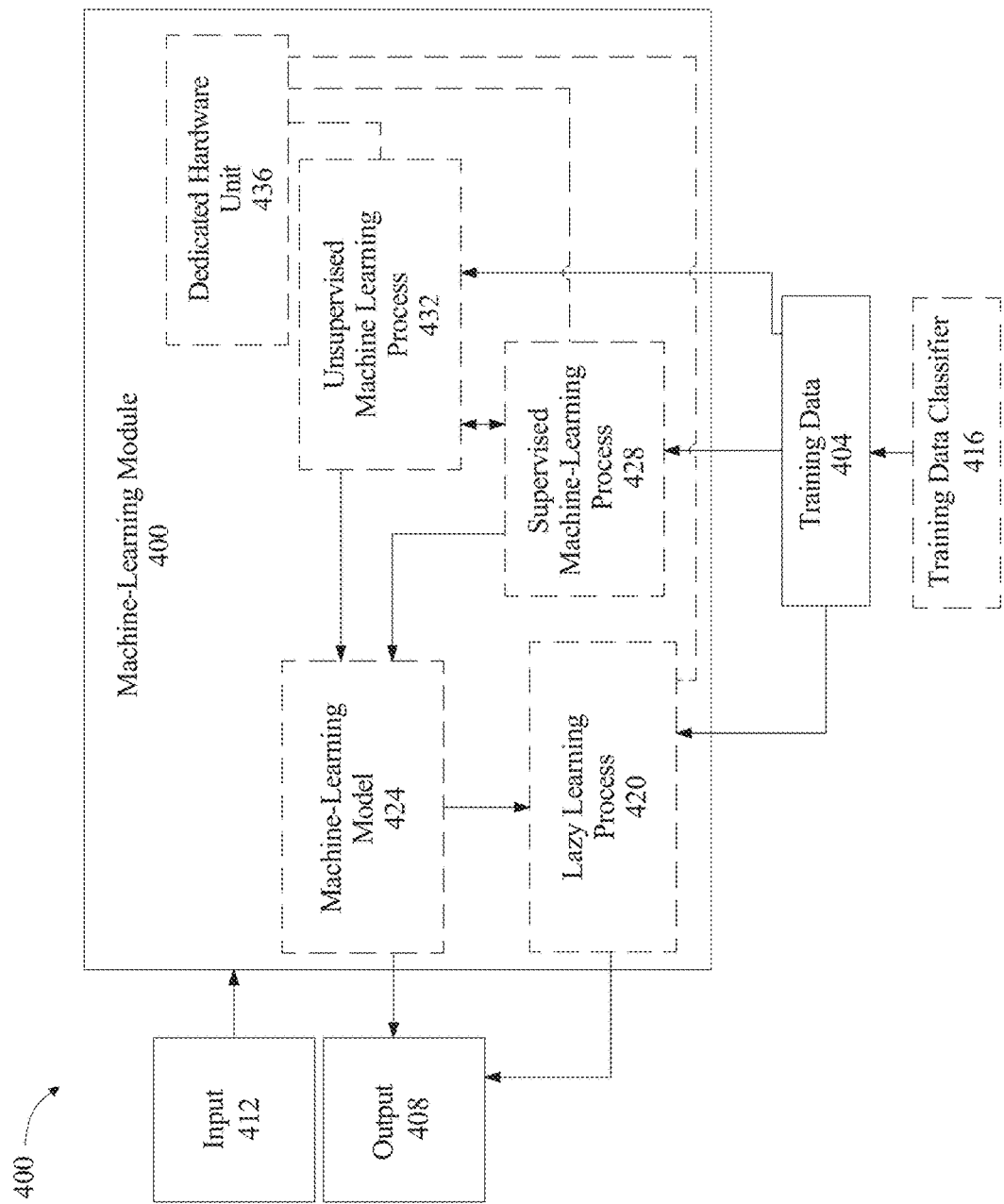
FIG. 4 is a block diagram of an exemplary embodiment of a machine learning process.

Referring now to FIG. 4, an exemplary embodiment of a machine learning module 400 that may perform one or more machine learning processes as described above is illustrated. Machine learning module may perform determinations, classification, and/or analysis steps, methods, processes, or the like as described in this disclosure using machine learning processes. For the purposes of this disclosure, a "machine learning process" is an automated process that uses training data 404 to generate an algorithm instantiated in hardware or software logic, data structures, and/or functions that will be performed by a computing device/module to produce outputs 408 given data provided as inputs 412. This is in contrast to a non-machine learning software program where the commands to be executed are pre-determined by a user and written in a programming language.

With continued reference to FIG. 4, "training data", for the purposes of this disclosure, are data containing correlations that a machine learning process uses to model relationships between two or more categories of data elements. For instance, and without limitation, training data 404 may include a plurality of data entries, also known as "training examples", each entry representing a set of data elements that were recorded, received, and/or generated together. Data elements may be correlated by shared existence in a given data entry, by proximity in a given data entry, or the like. Multiple data entries in training data 404 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 404 according to various correlations; correlations may indicate causative and/or predictive links between categories of data elements, which may be modeled as relationships such as mathematical relationships by machine learning processes as described in further detail below. Training data 404 may be formatted and/or organized by categories of data elements, for instance by associating data elements with one or more descriptors corresponding to categories of data elements. As a nonlimiting example, training data 404 may include data entered in standardized forms by persons or processes, such that entry of a given data element within a given field in a given form may be mapped to one or more descriptors of categories. Elements in training data 404 may be linked to descriptors of categories by tags, tokens, or other data elements. For instance, and without limitation, training data 404 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

With continued reference to FIG. 4, alternatively or additionally, training data 404 may include one or more elements that are uncategorized; that is, training data 404 may not be formatted or contain descriptors for some elements of data. Machine learning algorithms and/or other processes may sort training data 404 according to one or more categorizations using, for instance, natural language processing algorithms, tokenization, detection of correlated values in raw data, and the like; categories may be generated using correlation and/or other processing algorithms. As a nonlimiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine learning algorithms, and/or automated association of data in the data entry with descriptors or into a given format. The ability to categorize data entries automatedly may enable the same training data 404 to be made applicable for two or more distinct machine learning algorithms as described in further detail below. Training data 404 used by machine learning module 400 may correlate any input data as described in this disclosure to any output data as described in this disclosure. As a nonlimiting illustrative example, inputs may include plurality of exemplary medical images and plurality of exemplary electrograms, whereas outputs may include plurality of exemplary electro-anatomical mappings.

With continued reference to FIG. 4, training data 404 may be filtered, sorted, and/or selected using one or more supervised and/or unsupervised machine learning processes and/or models as described in further detail below; such processes and/or models may include without limitation a training data classifier 416. For the purposes of this disclosure, a "classifier" is a machine learning model that sorts inputs into categories or bins of data, outputting the categories or bins of data and/or labels associated therewith. Machine learning model may include without limitation a data structure representing and/or using a mathematical model, neural net, or a program generated by a machine learning algorithm, known as a "classification algorithm". A classifier may be configured to output at least a datum that labels or otherwise identifies a set of data that are clustered together, found to be close under a distance metric as described below, or the like. A distance metric may include any norm, such as, without limitation, a Pythagorean norm. Machine learning module 400 may generate a classifier using a classification algorithm. For the purposes of this disclosure, a "classification algorithm" is a process wherein a computing device and/or any module and/or component operating therein derives a classifier from training data 404. Classification may be performed using, without limitation, linear classifiers such as without limitation logistic regression and/or naive Bayes classifiers, nearest neighbor classifiers such as k-nearest neighbors classifiers, support vector machines, least squares support vector machines, Fisher's linear discriminant, quadratic classifiers, decision trees, boosted trees, random forest classifiers, learning vector quantization, and/or neural network-based classifiers. In one or more embodiments, training data classifier 416 may classify elements of training data to a plurality of cohorts as a function of certain anatomic traits.

With continued reference to FIG. 4, machine learning module 400 may be configured to generate a classifier using a naive Bayes classification algorithm. Naive Bayes classification algorithm generates classifiers by assigning class labels to problem instances, represented as vectors of element values. Class labels are drawn from a finite set. Naive Bayes classification algorithm may include generating a family of algorithms that assume that the value of a particular element is independent of the value of any other element, given a class variable. Naive Bayes classification algorithm may be based on Bayes Theorem expressed as P(A/B)=P(B/A)×P(A)÷P(B), where P(A/B) is the probability of hypothesis A given data B, also known as posterior probability; P(B/A) is the probability of data B given that the hypothesis A was true; P(A) is the probability of hypothesis A being true regardless of data, also known as prior probability of A; and P(B) is the probability of the data regardless of the hypothesis. A naive Bayes algorithm may be generated by first transforming training data into a frequency table. Machine learning module 400 may then calculate a likelihood table by calculating probabilities of different data entries and classification labels. Machine learning module 400 may utilize a naive Bayes equation to calculate a posterior probability for each class. A class containing the highest posterior probability is the outcome of prediction. Naive Bayes classification algorithm may include a gaussian model that follows a normal distribution. Naive Bayes classification algorithm may include a multinomial model that is used for discrete counts. Naive Bayes classification algorithm may include a Bernoulli model that may be utilized when vectors are binary.

With continued reference to FIG. 4, machine learning module 400 may be configured to generate a classifier using a k-nearest neighbors (KNN) algorithm. For the purposes of this disclosure, a "k-nearest neighbors algorithm" is or at least includes a classification method that utilizes feature similarity to analyze how closely out-of-sample features resemble training data 404 and to classify input data to one or more clusters and/or categories of features as represented in training data 404. This may be performed by representing both training data 404 and input data in vector forms and using one or more measures of vector similarity to identify classifications within training data 404 and determine a classification of input data. K-nearest neighbors algorithm may include specifying a k-value, or a number directing the classifier to select the k most similar entries of training data 404 to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a nonlimiting example, an initial heuristic may include a ranking of associations between inputs 412 and elements of training data 404. Heuristic may include selecting some number of highest-ranking associations and/or training data elements.

With continued reference to FIG. 4, generating k-nearest neighbors algorithm may generate a first vector output containing a data entry cluster, generating a second vector output containing input data, and calculate the distance between the first vector output and the second vector output using any suitable norm such as cosine similarity, Euclidean distance measurement, or the like. Each vector output may be represented, without limitation, as an n-tuple of values, where n is at least 2. Each value of n-tuple of values may represent a measurement or other quantitative value associated with a given category of data or attribute, examples of which are provided in further detail below. A vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent when their directions and/or relative quantities of values are the same; thus, as a nonlimiting example, a vector represented as [5, 10, 15] may be treated as equivalent, for the purposes of this disclosure, as a vector represented as [1, 2, 3]. Vectors may be more similar where their directions are more similar, and more different where their directions are more divergent. However, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized", or divided by a "length" attribute, such as a length attribute las derived using a $$\text{Pythagorean norm:} \ l = \sqrt{\sum_{i=0}^{n} a_i^2},$$

where $a_i$ is attribute number of vector i. Scaling and/or normalization may function to make vector comparison independent of absolute quantities of attributes, while preserving any dependency on similarity of attributes. This may, for instance, be advantageous where cases represented in training data 404 are represented by different quantities of samples, which may result in proportionally equivalent vectors with divergent values.

With continued reference to FIG. 4, training examples for use as training data may be selected from a population of potential examples according to cohorts relevant to an analytical problem to be solved, a classification task, or the like. Alternatively, or additionally, training data 404 may be selected to span a set of likely circumstances or inputs for a machine learning model and/or process to encounter when deployed. For instance, and without limitation, for each category of input data to a machine learning model and/or process that may exist in a range of values in a population of phenomena such as images, user data, process data, physical data, or the like, a computing device, processor 102, and/or machine learning module 400 may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively, or additionally, a set of training examples may be compared to a collection of representative values in a database and/or presented to user, so that a process can detect, automatically or via user input, one or more values that are not included in the set of training examples. Computing device, processor 102, and/or machine learning module 400 may automatically generate a missing training example. This may be done by receiving and/or retrieving a missing input and/or output value and correlating the missing input and/or output value with a corresponding output and/or input value collocated in a data record with the retrieved value, provided by user, another device, or the like.

With continued reference to FIG. 4, computing device, processor 102, and/or machine learning module 400 may be configured to preprocess training data 404. For the purposes of this disclosure, "preprocessing" training data is a process that transforms training data from a raw form to a format that can be used for training a machine learning model. Preprocessing may include sanitizing, feature selection, feature scaling, data augmentation and the like.

With continued reference to FIG. 4, computing device, processor 102, and/or machine learning module 400 may be configured to sanitize training data. For the purposes of this disclosure, "sanitizing" training data is a process whereby training examples that interfere with convergence of a machine learning model and/or process are removed to yield a useful result. For instance, and without limitation, a training example may include an input and/or output value that is an outlier from typically encountered values, such that a machine learning algorithm using the training example will be skewed to an unlikely range of input 412 and/or output 408; a value that is more than a threshold number of standard deviations away from an average, mean, or expected value, for instance, may be eliminated. Alternatively, or additionally, one or more training examples may be identified as having poor-quality data, where "poor-quality" means having a signal-to-noise ratio below a threshold value. In one or more embodiments, sanitizing training data may include steps such as removing duplicative or otherwise redundant data, interpolating missing data, correcting data errors, standardizing data, identifying outliers, and/or the like. In one or more embodiments, sanitizing training data may include algorithms that identify duplicate entries or spell-check algorithms.

With continued reference to FIG. 4, in one or more embodiments, images used to train an image classifier or other machine learning model and/or process that takes images as inputs 412 or generates images as outputs 408 may be rejected if image quality is below a threshold value. For instance, and without limitation, computing device, processor 102, and/or machine learning module 400 may perform blur detection. Elimination of one or more blurs may be performed, as a nonlimiting example, by taking Fourier transform or a Fast Fourier Transform (FFT) of image and analyzing a distribution of low and high frequencies in the resulting frequency-domain depiction of the image. Numbers of high-frequency values below a threshold level may indicate blurriness. As a further nonlimiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of image, based on the hypothesis that rapid changes indicate sharp edges in the image, and thus are indicative of a lower degree of blurriness. Blur detection may be performed using a wavelet-based operator, which uses coefficients of a discrete wavelet transform to describe the frequency and spatial content of images. Blur detection may be performed using statistics-based operators that take advantage of several image statistics as texture descriptors in order to compute a focus level. Blur detection may be performed by using discrete cosine transform (DCT) coefficients in order to compute a focus level of an image from its frequency content.

With continued reference to FIG. 4, computing device, processor 102, and/or machine learning module 400 may be configured to precondition one or more training examples. For instance, and without limitation, where a machine learning model and/or process has one or more inputs 412 and/or outputs 408 requiring, transmitting, or receiving a certain number of bits, samples, or other units of data, one or more elements of training examples to be used as or compared to inputs 412 and/or outputs 408 may be modified to have such a number of units of data. In one or more embodiments, computing device, processor 102, and/or machine learning module 400 may convert a smaller number of units, such as in a low pixel count image, into a desired number of units by upsampling and interpolating. As a nonlimiting example, a low pixel count image may have 100 pixels, whereas a desired number of pixels may be 128. Processor 102 may interpolate the low pixel count image to convert 100 pixels into 128 pixels. It should also be noted that one of ordinary skill in the art, upon reading the entirety of this disclosure, would recognize the various methods to interpolate a smaller number of data units such as samples, pixels, bits, or the like to a desired number of such units. In one or more embodiments, a set of interpolation rules may be trained by sets of highly detailed inputs 412 and/or outputs 408 and corresponding inputs 412 and/or outputs 408 downsampled to smaller numbers of units, and a neural network or another machine learning model that is trained to predict interpolated pixel values using the training data 404. As a nonlimiting example, a sample input 412 and/or output 408, such as a sample picture, with sample-expanded data units (e.g., pixels added between the original pixels) may be input to a neural network or machine learning model and output a pseudo replica sample picture with dummy values assigned to pixels between the original pixels based on a set of interpolation rules. As a nonlimiting example, in the context of an image classifier, a machine learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively, or additionally, computing device, processor 102, and/or machine learning module 400 may utilize sample expander methods, a low-pass filter, or both. For the purposes of this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor 102, and/or machine learning module 400 may use averaging, such as luma or chroma averaging in images, to fill in data units in between original data units.

With continued reference to FIG. 4, in one or more embodiments, computing device, processor 102, and/or machine learning module 400 may downsample elements of a training example to a desired lower number of data elements. As a nonlimiting example, a high pixel count image may contain 256 pixels, however a desired number of pixels may be 128. Processor 102 may downsample the high pixel count image to convert 256 pixels into 128 pixels. In one or more embodiments, processor 102 may be configured to perform downsampling on data. Downsampling, also known as decimation, may include removing every $N^{th}$ entry in a sequence of samples, all but every $N^{th}$ entry, or the like, which is a process known as "compression" and may be performed, for instance by an N-sample compressor implemented using hardware or software. Anti-aliasing and/or anti-imaging filters, and/or low-pass filters, may be used to eliminate side effects of compression.

With continued reference to FIG. 4, feature selection may include narrowing and/or filtering training data 404 to exclude features and/or elements, or training data including such elements that are not relevant to a purpose for which a trained machine learning model and/or algorithm is being trained, and/or collection of features, elements, or training data including such elements based on relevance to or utility for an intended task or purpose for which a machine learning model and/or algorithm is being trained. Feature selection may be implemented, without limitation, using any process described in this disclosure, including without limitation using training data classifiers, exclusion of outliers, or the like.

With continued reference to FIG. 4, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, wherein a difference between each value, X, and a minimum value, $X_{min}$, in a set or subset of values is divided by a range of values, $X_{max}-X_{min}$, in the set or subset:

$$X_{new} = \frac{X - X_{min}}{X_{max} - X_{min}}.$$

Feature scaling may include mean normalization, wherein a difference between each value, X, and a mean value of a set and/or subset of values, $X_{mean}$, is divided by a range of values, $X_{max}-X_{min}$, in the set or subset:

$$X_{new} = \frac{X - X_{mean}}{X_{max} - X_{min}}.$$

Feature scaling may include standardization, wherein a difference between X and $X_{mean}$ is divided by a standard deviation, $\sigma$, of a set or subset of values:

$$X_{new} = \frac{X - X_{mean}}{\sigma}.$$

Feature scaling may be performed using a median value of a set or subset, $X_{median}$, and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

A Person of ordinary skill in the art, upon reviewing the entirety of this disclosure, will be aware of various alternative or additional approaches that may be used for feature scaling.

With continued reference to FIG. 4, computing device, processor 102, and/or machine learning module 400 may be configured to perform one or more processes of data augmentation. For the purposes of this disclosure, "data augmentation" is a process that adds data to a training data 404 using elements and/or entries already in the dataset. Data augmentation may be accomplished, without limitation, using interpolation, generation of modified copies of existing entries and/or examples, and/or one or more generative artificial intelligence (AI) processes, for instance using deep neural networks and/or generative adversarial networks. Generative processes may be referred to alternatively in this context as "data synthesis" and as creating "synthetic data". Augmentation may include performing one or more transformations on data, such as geometric, color space, affine, brightness, cropping, and/or contrast transformations of images.

With continued reference to FIG. 4, machine learning module 400 may be configured to perform a lazy learning process and/or protocol 420. For the purposes of this disclosure, a "lazy learning" process and/or protocol is a process whereby machine learning is conducted upon receipt of input 412 to be converted to output 408 by combining the input 412 and training data 404 to derive the algorithm to be used to produce the output 408 on demand. A lazy learning process may alternatively be referred to as a "lazy loading" or "call-when-needed" process and/or protocol. For instance, an initial set of simulations may be performed to cover an initial heuristic and/or "first guess" at an output 408 and/or relationship. As a nonlimiting example, an initial heuristic may include a ranking of associations between inputs 412 and elements of training data 404. Heuristic may include selecting some number of highest-ranking associations and/or training data 404 elements. Lazy learning may implement any suitable lazy learning algorithm, including without limitation a k-nearest neighbors algorithm, a lazy naive Bayes algorithm, or the like. A person of ordinary skill in the art, upon reviewing the entirety of this disclosure, will be aware of various lazy learning algorithms that may be applied to generate outputs as described in this disclosure, including without limitation lazy learning applications of machine learning algorithms as described in further detail below.

With continued reference to FIG. 4, alternatively, or additionally, machine learning processes as described in this disclosure may be used to generate machine learning models 424. A "machine learning model", for the purposes of this disclosure, is a data structure representing and/or instantiating a mathematical and/or algorithmic representation of a relationship between inputs 412 and outputs 408, generated using any machine learning process including without limitation any process described above, and stored in memory. An input 412 is submitted to a machine learning model 424 once created, which generates an output 408 based on the relationship that was derived. For instance, and without limitation, a linear regression model, generated using a linear regression algorithm, may compute a linear combination of input data using coefficients derived during machine learning processes to calculate an output datum. As a further nonlimiting example, a machine learning model 424 may be generated by creating an artificial neural network, such as a convolutional neural network comprising an input layer of nodes, one or more intermediate layers, and an output layer of nodes. Connections between nodes may be created by "training" the network, in which elements from a training data 404 are applied to the input nodes, and a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning, as described in detail below.

With continued reference to FIG. 4, machine learning module 400 may perform at least a supervised machine learning process 428. For the purposes of this disclosure, a "supervised" machine learning process is a process with algorithms that receive training data 404 relating one or more inputs 412 to one or more outputs 408, and seek to generate one or more data structures representing and/or instantiating one or more mathematical relations relating input 412 to output 408, where each of the one or more mathematical relations is optimal according to some criterion specified to the algorithm using some scoring function. For instance, a supervised learning algorithm may include inputs 412 described above as inputs, and outputs 408 described above as outputs, and a scoring function representing a desired form of relationship to be detected between inputs 412 and outputs 408. Scoring function may, for instance, seek to maximize the probability that a given input 412 and/or combination thereof is associated with a given output 408 to minimize the probability that a given input 412 is not associated with a given output 408. Scoring function may be expressed as a risk function representing an "expected loss" of an algorithm relating inputs 412 to outputs 408, where loss is computed as an error function representing a degree to which a prediction generated by the relation is incorrect when compared to a given input-output pair provided in training data 404. Supervised machine learning processes may include classification algorithms as defined above. A person of ordinary skill in the art, upon reviewing the entirety of this disclosure, will be aware of various possible variations of at least a supervised machine learning process 428 that may be used to determine a relation between inputs and outputs.

With continued reference to FIG. 4, training a supervised machine learning process may include, without limitation, iteratively updating coefficients, biases, and weights based on an error function, expected loss, and/or risk function. For instance, an output 408 generated by a supervised machine learning process 428 using an input example in a training example may be compared to an output example from the training example; an error function may be generated based on the comparison, which may include any error function suitable for use with any machine learning algorithm described in this disclosure, including a square of a difference between one or more sets of compared values or the like. Such an error function may be used in turn to update one or more weights, biases, coefficients, or other parameters of a machine learning model through any suitable process including without limitation gradient descent processes, least-squares processes, and/or other processes described in this disclosure. This may be done iteratively and/or recursively to gradually tune such weights, biases, coefficients, or other parameters. Updates may be performed in neural networks using one or more back-propagation algorithms. Iterative and/or recursive updates to weights, biases, coefficients, or other parameters as described above may be performed until currently available training data 404 are exhausted and/or until a convergence test is passed. For the purposes of this disclosure, a "convergence test" is a test for a condition selected to indicate that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively, or additionally, one or more errors and/or error function values evaluated in training iterations may be compared to a threshold.

With continued reference to FIG. 4, a computing device, processor 102, and/or machine learning module 400 may be configured to perform method, method step, sequence of method steps, and/or algorithm described in reference to this figure, in any order and with any degree of repetition. For instance, computing device, processor 102, and/or machine learning module 400 may be configured to perform a single step, sequence, and/or algorithm repeatedly until a desired or commanded outcome is achieved; repetition of a step or a sequence of steps may be performed iteratively and/or recursively using outputs 408 of previous repetitions as inputs 412 to subsequent repetitions, aggregating inputs 412 and/or outputs 408 of repetitions to produce an aggregate result, reduction or decrement of one or more variables such as global variables, and/or division of a larger processing task into a set of iteratively addressed smaller processing tasks. A computing device, processor 102, apparatus 100, or machine learning module 400 may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. A person of ordinary skill in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 4, machine learning process may include at least an unsupervised machine learning process 432. For the purposes of this disclosure, an unsupervised machine learning process is a process that derives inferences in datasets without regard to labels. As a result, an unsupervised machine learning process 432 may be free to discover any structure, relationship, and/or correlation provided in the data. Unsupervised processes 432 may not require a response variable, may be used to find interesting patterns and/or inferences between variables, to determine a degree of correlation between two or more variables, or the like.

With continued reference to FIG. 4, machine learning module 400 may be designed and configured to create machine learning model 424 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include an elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to a person of ordinary skill in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought. Similar methods to those described above may be applied to minimize error functions, as will be apparent to a person of ordinary skill in the art upon reviewing the entirety of this disclosure.

With continued reference to FIG. 4, machine learning algorithms may include, without limitation, linear discriminant analysis. Machine learning algorithm may include quadratic discriminant analysis. Machine learning algorithms may include kernel ridge regression. Machine learning algorithms may include support vector machines, including without limitation support vector classification-based regression processes. Machine learning algorithms may include stochastic gradient descent algorithms, including classification and regression algorithms based on stochastic gradient descent. Machine learning algorithms may include nearest neighbors algorithms. Machine learning algorithms may include various forms of latent space regularization such as variational regularization. Machine learning algorithms may include Gaussian processes such as Gaussian Process Regression. Machine learning algorithms may include cross-decomposition algorithms, including partial least squares and/or canonical correlation analysis. Machine learning algorithms may include naive Bayes methods. Machine learning algorithms may include algorithms based on decision trees, such as decision tree classification or regression algorithms. Machine learning algorithms may include ensemble methods such as bagging meta-estimator, forest of randomized trees, AdaBoost, gradient tree boosting, and/or voting classifier methods. Machine learning algorithms may include neural net algorithms, including convolutional neural net processes.

With continued reference to FIG. 4, a machine learning model and/or process may be deployed or instantiated by incorporation into a program, apparatus, system, and/or module. For instance, and without limitation, a machine learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit, to represent a number according to any suitable encoding system including twos complement or the like, or may be stored in any volatile and/or non-volatile memory. Similarly, mathematical operations and input 412 and/or output 408 of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine learning process and/or model, including without limitation any combination of production and/or configuration of non-reconfigurable hardware elements, circuits, and/or modules such as without limitation application-specific integrated circuits (ASICs), production and/or configuration of reconfigurable hardware elements, circuits, and/or modules such as without limitation field programmable gate arrays (FPGAs), production and/or configuration of non-reconfigurable and/or non-rewritable memory elements, circuits, and/or modules such as without limitation non-rewritable read-only memory (ROM), other memory technology described in this disclosure, and/or production and/or configuration of any computing device and/or component thereof as described in this disclosure. Such deployed and/or instantiated machine learning model and/or algorithm may receive inputs 412 from any other process, module, and/or component described in this disclosure, and produce outputs 408 to any other process, module, and/or component described in this disclosure.

With continued reference to FIG. 4, any process of training, retraining, deployment, and/or instantiation of any machine learning model and/or algorithm may be performed and/or repeated after an initial deployment and/or instantiation to correct, refine, and/or improve the machine learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively, or additionally, retraining, deployment, and/or instantiation may be event-based, and may be triggered, without limitation, by user inputs indicating sub-optimal or otherwise problematic performance and/or by automated field testing and/or auditing processes, which may compare outputs 408 of machine learning models and/or algorithms, and/or errors and/or error functions thereof, to any thresholds, convergence tests, or the like, and/or may compare outputs 408 of processes described herein to similar thresholds, convergence tests or the like. Event-based retraining, deployment, and/or instantiation may alternatively, or additionally, be triggered by receipt and/or generation of one or more new training examples; a number of new training examples may be compared to a preconfigured threshold, where exceeding the preconfigured threshold may trigger retraining, deployment, and/or instantiation.

With continued reference to FIG. 4, retraining and/or additional training may be performed using any process for training described above, using any currently or previously deployed version of a machine learning model and/or algorithm as a starting point. Training data for retraining may be collected, preconditioned, sorted, classified, sanitized, or otherwise processed according to any process described in this disclosure. Training data 404 may include, without limitation, training examples including inputs 412 and correlated outputs 408 used, received, and/or generated from any version of any system, module, machine learning model or algorithm, apparatus, and/or method described in this disclosure. Such examples may be modified and/or labeled according to user feedback or other processes to indicate desired results, and/or may have actual or measured results from a process being modeled and/or predicted by system, module, machine learning model or algorithm, apparatus, and/or method as "desired" results to be compared to outputs 408 for training processes as described above. Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

With continued reference to FIG. 4, one or more processes or algorithms described above may be performed by at least a dedicated hardware unit 436. For the purposes of this disclosure, a "dedicated hardware unit" is a hardware component, circuit, or the like, aside from a principal control circuit and/or processor 102 performing method steps as described in this disclosure, that is specifically designated or selected to perform one or more specific tasks and/or processes described in reference to this figure. Such specific tasks and/or processes may include without limitation preprocessing and/or sanitization of training data and/or training a machine learning algorithm and/or model. Dedicated hardware unit 436 may include, without limitation, a hardware unit that can perform iterative or massed calculations, such as matrix-based calculations to update or tune parameters, weights, coefficients, and/or biases of machine learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously, in parallel, and/or the like. Such dedicated hardware units 436 may include, without limitation, graphical processing units (GPUs), dedicated signal processing modules, field programmable gate arrays (FPGA), other reconfigurable hardware that has been configured to instantiate parallel processing units for one or more specific tasks, or the like. Computing device, processor 102, apparatus 100, or machine learning module 400 may be configured to instruct one or more dedicated hardware units 436 to perform one or more operations described herein, such as evaluation of model and/or algorithm outputs, one-time or iterative updates to parameters, coefficients, weights, and/or biases, vector and/or matrix operations, and/or any other operations described in this disclosure.

Figure 5:
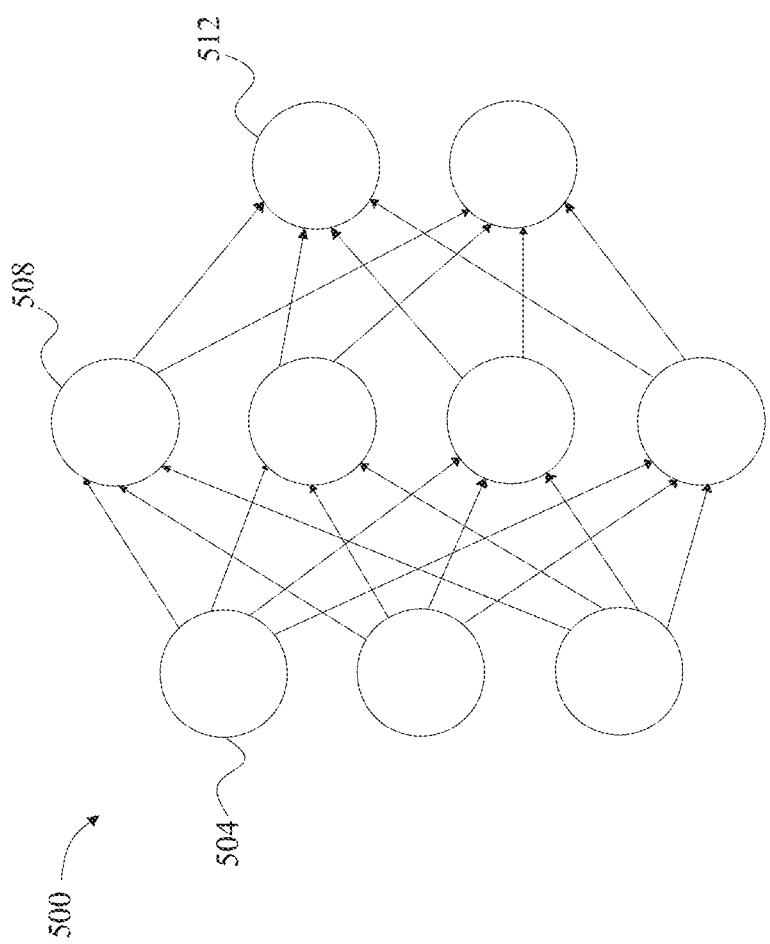
FIG. 5 is a block diagram of an exemplary embodiment of a neural network.

Referring now to FIG. 5, an exemplary embodiment of neural network 500 is illustrated. For the purposes of this disclosure, a neural network or artificial neural network is a network of "nodes" or data structures having one or more inputs, one or more outputs, and a function determining outputs based on inputs. Such nodes may be organized in a network, such as without limitation a convolutional neural network, including an input layer of nodes 504, at least an intermediate layer of nodes 508, and an output layer of nodes 512. Connections between nodes may be created via the process of "training" neural network 500, in which elements from a training dataset are applied to the input nodes, and a suitable training algorithm (such as Levenberg-Marquardt, conjugate gradient, simulated annealing, or other algorithms) is then used to adjust the connections and weights between nodes in adjacent layers of the neural network 500 to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network". As a further nonlimiting example, neural network 500 may include a convolutional neural network comprising an input layer of nodes 504, one or more intermediate layers of nodes 508, and an output layer of nodes 512. For the purposes of this disclosure, a "convolutional neural network" is a type of neural network 500 in which at least one hidden layer is a convolutional layer that convolves inputs to that layer with a subset of inputs known as a "kernel", along with one or more additional layers such as pooling layers, fully connected layers, and the like.

Figure 6:
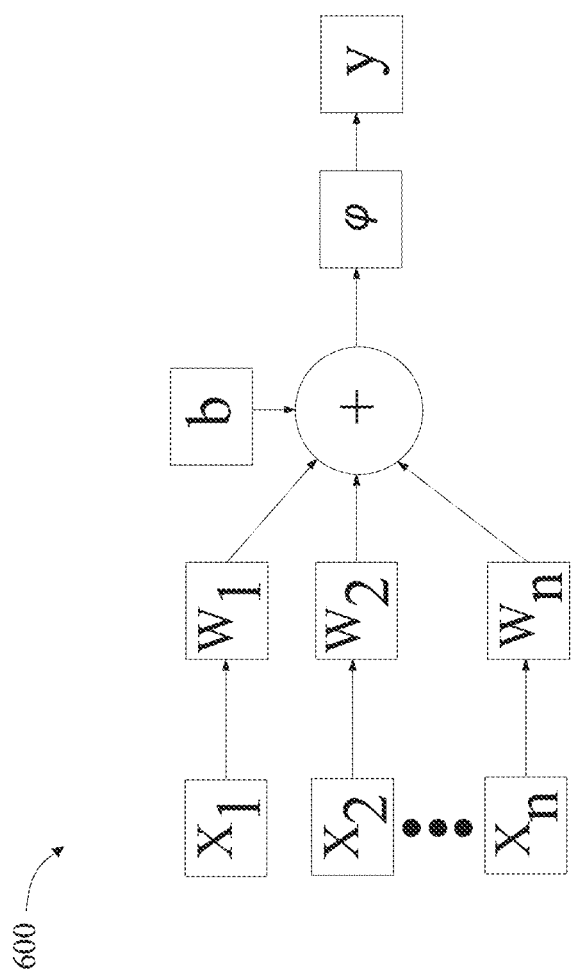
FIG. 6 is a block diagram of an exemplary embodiment of a node of a neural network.

Referring now to FIG. 6, an exemplary embodiment of a node 600 of neural network 500 is illustrated. Node 600 may include, without limitation, a plurality of inputs, $x_i$, that may receive numerical values from inputs to neural network 500 containing the node 600 and/or from other nodes 600. Node 600 may perform one or more activation functions to produce its output given one or more inputs, such as without limitation computing a binary step function comparing an input to a threshold value and outputting either a logic 1 or logic 0 output or its equivalent, a linear activation function whereby an output is directly proportional to input, and/or a nonlinear activation function wherein the output is not proportional to the input. Nonlinear activation functions may include, without limitation, a sigmoid function of the form $$f(x) = \frac{1}{1 - e^{-x}}$$

given input x, a tanh (hyperbolic tangent) function of the form $$\frac{e^x - e^{-x}}{e^x + e^{-x}},$$

a tanh derivative function such as $f(x) = \tanh^2(x)$, a rectified linear unit function such as $f(x) = \max(0, x)$, a "leaky" and/or "parametric" rectified linear unit function such as $f(x) = \max(ax, x)$ for some value of a, an exponential linear units function such as $$f(x) = \begin{cases} x & \text{for } x \geq 0 \\ \alpha(e^x - 1) & \text{for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x) = x \ast \text{sigmoid}(x)$, a Gaussian error linear unit function such as f(x)=a(1+tanh($\sqrt{2/\pi}$(x+bx$^r$))) for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs $x_i$, that may be used as activation functions. As a nonlimiting and illustrative example, node 600 may perform a weighted sum of inputs using weights, $w_i$, that are multiplied by respective inputs, $x_i$. Additionally, or alternatively, a bias b may be added to the weighted sum of the inputs such that an offset is added to each unit in a neural network layer that is independent of the input to the layer. The weighted sum may then be input into a function, q, which may generate one or more outputs, y. Weight, $w_i$, applied to an input, $x_i$, may indicate whether the input is "excitatory", indicating that it has strong influence on the one or more outputs, y, for instance by the corresponding weight having a large numerical value, or "inhibitory", indicating it has a weak influence on the one more outputs, y, for instance by the corresponding weight having a small numerical value. The values of weights, $w_i$, may be determined by training neural network 500 using training data, which may be performed using any suitable process as described above.

Figure 7:
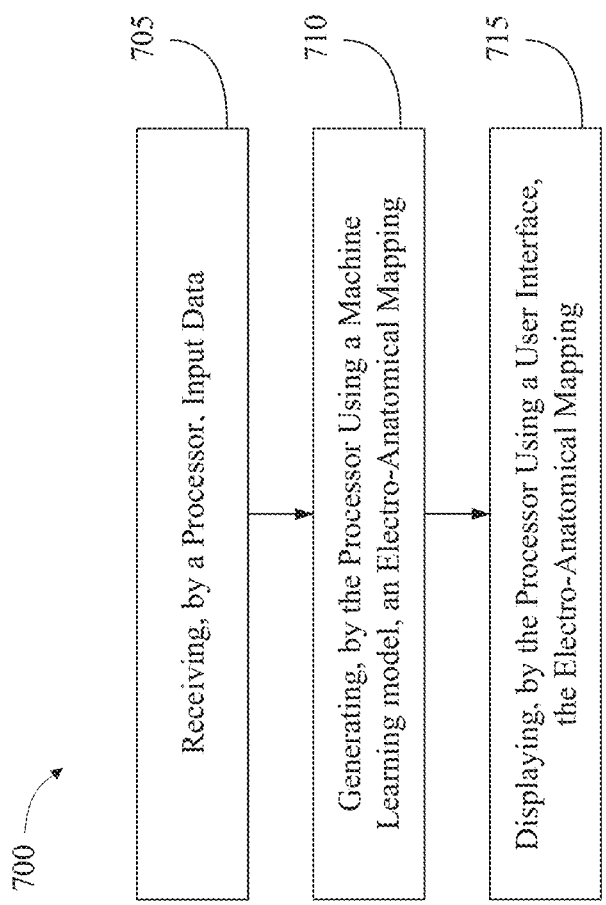
FIG. 7 is an exemplary flow diagram illustrating a method for generating an electro-anatomical mapping.

Referring now to FIG. 7, an exemplary embodiment of a method 700 for generating electro-anatomical mapping 122 is described. At step 705, method 700 includes receiving, by processor 102, input data 106, wherein receiving the input data includes receiving, from imaging device 108, at least a medical image 110 and receiving, from signal capturing device 116, at least an electrogram 118. This step may be implemented with reference to details described above in this disclosure and without limitation.

With continued reference to FIG. 7, at step 710, method 700 includes generating, by processor 102 using at least a machine learning model 124, electro-anatomical mapping 122 as a function of input data 106, wherein the at least a machine learning model 124 is trained using electro-anatomical mapping training data 126 including exemplary medical images and exemplary electrograms as input correlated to exemplary electro-anatomical mappings as output. This step may be implemented with reference to details described above in this disclosure and without limitation.

With continued reference to FIG. 7, at step 715, method 700 includes displaying, by processor 102 using user interface 138, electro-anatomical mapping 122. This step may be implemented with reference to details described above in this disclosure and without limitation.

Figure 8:
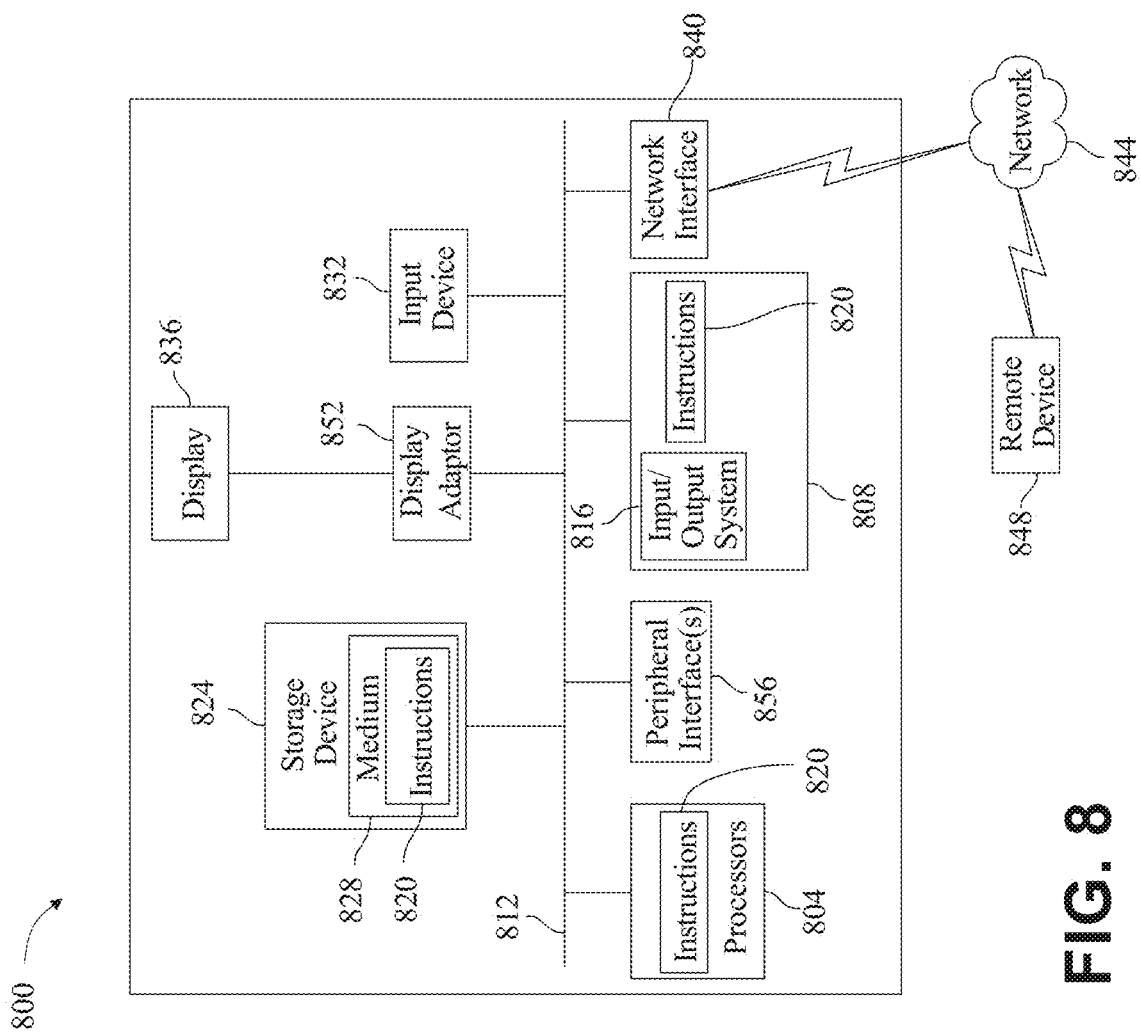
FIG. 8 is a block diagram of an exemplary embodiment of a computing system that can be used to implement any one or more of the methodologies disclosed herein and any one or more portions thereof.

Referring now to FIG. 8, it is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to one of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module. Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission. Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein. Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

With continued reference to FIG. 8, the figure shows a diagrammatic representation of one embodiment of a computing device in the exemplary form of a computing system 800 within which a set of instructions for causing the computing system 800 to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computing system 800 may include a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures. Processor 804 may include any suitable processor, such as without limitation a processor incorporating logical circuitry for performing arithmetic and logical operations, such as an arithmetic and logic unit, which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor, field programmable gate array, complex programmable logic device, graphical processing unit, general-purpose graphical processing unit, tensor processing unit, analog or mixed signal processor, trusted platform module, a floating-point unit, and/or system on a chip.

With continued reference to FIG. 8, memory 808 may include various components (e.g., machine-readable media) including, but not limited to, a random-access memory component, a read only component, and any combinations thereof. In one example, a basic input/output system 816, including basic routines that help to transfer information between elements within computing system 800, such as during start-up, may be stored in memory 808. Memory 808 (e.g., stored on one or more machine-readable media) may also include instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

With continued reference to FIG. 8, computing system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, small computer system interface, advanced technology attachment, serial advanced technology attachment, universal serial bus, IEEE 1394 (FIREWIRE), and any combinations thereof. In one example, storage device 824 (or one or more components thereof) may be removably interfaced with computing system 800 (e.g., via an external port connector (not shown)). Particularly, storage device 824 and an associated machine-readable medium 828 may provide nonvolatile and/or volatile storage of machine-readable instructions, data structures, program modules, and/or other data for computing system 800. In one example, software 820 may reside, completely or partially, within machine-readable medium 828. In another example, software 820 may reside, completely or partially, within processor 804.

With continued reference to FIG. 8, computing system 800 may also include an input device 832. In one example, a user of computing system 800 may enter commands and/or other information into computing system 800 via input device 832. Examples of input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display device 836, discussed further below. Input device 832 may be utilized as a user selection device for selecting one or more graphical representations in a graphical interface as described above.

With continued reference to FIG. 8, user may also input commands and/or other information to computing system 800 via storage device 824 (e.g., a removable disk drive, a flash drive, etc.) and/or network interface device 840. A network interface device, such as network interface device 840, may be utilized for connecting computing system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide-area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computing system 800 via network interface device 840.

With continued reference to FIG. 8, computing system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computing system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for generating electro-anatomical mapping, the apparatus comprising: a processor; and a memory communicatively connected to the processor, wherein the memory contains instructions configuring the processor to: receive input data, wherein receiving the input data comprises: receiving, from an imaging device, at least a medical image; and receiving, from a signal capturing device, at least an electrogram; generate, using at least a machine learning model, an electro-anatomical mapping as a function of the input data, wherein the at least a machine learning model is trained using electro-anatomical mapping training data comprising exemplary medical images and exemplary electrograms as input correlated to exemplary electro-anatomical mappings as output; and display the electro-anatomical mapping using a user interface, wherein generating the electro-anatomical mapping comprises: generating a putative electro-anatomical mapping; validating the putative electro-anatomical mapping using a plurality of quality assurance parameters; and creating the electro-anatomical mapping by fine-tuning the putative electro-anatomical mapping as a function of an outcome of the validation.

2. The apparatus of claim 1, wherein the at least a medical image comprises one or more of at least a computed tomography (CT) scan and at least a magnetic resonance imaging (MRI) scan.

3. The apparatus of claim 1, wherein the at least an electrogram comprises at least an electrocardiogram (ECG).

4. The apparatus of claim 1, wherein the input data further comprises one or more members from a group consisting of ultrasound data, point-of-care ultrasound (POCUS) data, intravascular ultrasound data, abdominal ultrasound data, at least a transthoracic echocardiogram (TTE), at least a transesophageal echocardiogram (TEE), at least an intracardiac echocardiogram (ICE), and at least a stress echocardiogram.

5. The apparatus of claim 1, wherein the processor is further configured to:
identify at least a target location pertaining to a medical procedure within the electro-anatomical mapping; and
highlight the at least a target location within the electro-anatomical mapping using the user interface.

6. The apparatus of claim 5, wherein:
the medical procedure comprises an ablation procedure; and
the electro-anatomical mapping is used as an initial mapping for the ablation procedure.

7. The apparatus of claim 6, wherein the processor is further configured to:
receive, from a navigation system, a location of a catheter; and
display, using the user interface, the location of the catheter on the electro-anatomical mapping.

8. The apparatus of claim 7, wherein the processor is further configured modify the electro-anatomical mapping as a function of the location of the catheter.

9. The apparatus of claim 5, wherein the processor is further configured to:
identify at least a medical feature within the electro-anatomical mapping; and
adjust at least a parameter pertaining to the medical procedure as a function of the at least a medical feature.

10. The apparatus of claim 1, wherein generating the electro-anatomical mapping comprises aligning an electrical mapping with an anatomical mapping using fiducial point-based registration.

11. The apparatus of claim 1, wherein the electro-anatomical mapping comprises a color-coded heat map.

12. The apparatus of claim 1, wherein:
the exemplary medical images comprise historical medical images pertaining to a plurality of entities and collected prior to one or more historical medical procedures;
the exemplary electrograms comprise historical electrograms pertaining to the plurality of entities, wherein the historical electrograms are collected prior to the one or more historical medical procedures and temporally correlated with the exemplary medical images; and
the exemplary electro-anatomical mappings comprise historical electro-anatomical mappings pertaining to the plurality of entities and collected during the one or more historical medical procedures.

13. The apparatus of claim 12, wherein:
the historical medical images comprise one or more of historical CT scans, historical MRI scans, and historical ultrasound data;
the historical electrograms comprise historical ECGs; and
the historical electro-anatomical mappings comprise historical cardiac electro-anatomical mappings pertaining to one or more ablation procedures.

14. A method for generating electro-anatomical mapping, the method comprising: receiving, by a processor, input data, wherein receiving the input data comprises: receiving, from an imaging device, at least a medical image; and receiving, from a signal capturing device, at least an electrogram; generating, by the processor using at least a machine learning model, an electro-anatomical mapping as a function of the input data, wherein the at least a machine learning model is trained using electro-anatomical mapping training data comprising exemplary medical images and exemplary electrograms as input correlated to exemplary electro-anatomical mappings as output; and displaying, by the processor using a user interface, the electro-anatomical mapping, wherein generating the electro-anatomical mapping comprises: generating a putative electro-anatomical mapping; validating the putative electro-anatomical mapping using a plurality of quality assurance parameters; and creating the electro-anatomical mapping by fine-tuning the putative electro-anatomical mapping as a function of an outcome of the validation.

15. The method of claim 14, wherein the at least a medical image comprises one or more of at least a computed tomography (CT) scan and at least a magnetic resonance imaging (MRI) scan.

16. The method of claim 14, wherein the at least an electrogram comprises at least an electrocardiogram (ECG).

17. The method of claim 14, wherein the input data further comprises one or more members from a group consisting of ultrasound data, point-of-care ultrasound (POCUS) data, intravascular ultrasound data, abdominal ultrasound data, at least a transthoracic echocardiogram (TTE), at least a transesophageal echocardiogram (TEE), at least an intracardiac echocardiogram (ICE), and at least a stress echocardiogram.

18. The method of claim 14, further comprising:
identifying, by the processor, at least a target location pertaining to a medical procedure within the electro-anatomical mapping; and
highlighting, by the processor, the at least a target location within the electro-anatomical mapping using the user interface.

19. The method of claim 18, wherein:
the medical procedure comprises an ablation procedure; and
the electro-anatomical mapping is used as an initial mapping for the ablation procedure.

20. The method of claim 19, further comprising:
receiving, by the processor from a navigation system, a location of a catheter; and
displaying, by the processor using the user interface, the location of the catheter on the electro-anatomical mapping.

21. The method of claim 20, further comprising modifying the electro-anatomical mapping as a function of the location of the catheter.

22. The method of claim 18, further comprising:
identifying, by the processor, at least a medical feature within the electro-anatomical mapping; and
adjusting, by the processor, at least a parameter pertaining to the medical procedure as a function of the at least a medical feature.

23. The method of claim 14, wherein generating the electro-anatomical mapping comprises aligning an electrical mapping with an anatomical mapping using fiducial point-based registration.

24. The method of claim 14, wherein the electro-anatomical mapping comprises a color-coded heat map.

25. The method of claim 14, wherein:
the exemplary medical images comprise historical medical images pertaining to a plurality of entities and collected prior to one or more historical medical procedures;
the exemplary electrograms comprise historical electrograms pertaining to the plurality of entities, wherein the historical electrograms are collected prior to the one or more historical medical procedures and temporally correlated with the exemplary medical images; and
the exemplary electro-anatomical mappings comprise historical electro-anatomical mappings pertaining to the plurality of entities and collected during the one or more historical medical procedures.

26. The method of claim 25, wherein:
the historical medical images comprise one or more of historical CT scans, historical MRI scans, and historical ultrasound data;
the historical electrograms comprise historical ECGs; and
the historical electro-anatomical mappings comprise historical cardiac electro-anatomical mappings pertaining to one or more ablation procedures.

* * * * *